(12) United States Patent
Nakatomi et al.

(10) Patent No.: US 12,094,106 B2
(45) Date of Patent: Sep. 17, 2024

(54) IMAGE PROCESSING DEVICE AND CULTURE EVALUATION SYSTEM

(71) Applicant: Evident Corporation, Nagano (JP)

(72) Inventors: Takayuki Nakatomi, Tokyo (JP); Isao Sakane, Tokyo (JP)

(73) Assignee: Evident Corporation, Nagano (JP)

( * ) Notice: Subject to any disclaimer, the term of this patent is extended or adjusted under 35 U.S.C. 154(b) by 854 days.

(21) Appl. No.: 17/101,170

(22) Filed: Nov. 23, 2020

(65) Prior Publication Data

US 2021/0142474 A1 May 13, 2021

Related U.S. Application Data

(63) Continuation of application No. PCT/JP2018/021816, filed on Jun. 7, 2018.

(51) Int. Cl.
*G06T 7/00* (2017.01)
*G01N 33/50* (2006.01)

(52) U.S. Cl.
CPC ....... *G06T 7/0012* (2013.01); *G01N 33/5005* (2013.01); *G06T 2207/30024* (2013.01); *G06T 2207/30242* (2013.01)

(58) Field of Classification Search
CPC ......... G06T 7/0012; G06T 2207/30024; G06T 2207/30242; G01N 33/5005; C12M 41/36
See application file for complete search history.

(56) References Cited

U.S. PATENT DOCUMENTS

| 5,031,099 A * | 7/1991 | Kettler | G01N 15/1468 382/133 |
| 2010/0232675 A1* | 9/2010 | Ortyn | A61B 1/00188 382/134 |
| 2011/0013821 A1* | 1/2011 | Mimura | G06T 7/0016 382/133 |
| 2011/0092762 A1 | 4/2011 | Wong et al. | |
| 2011/0105834 A1 | 5/2011 | Wong et al. | |
| 2012/0094326 A1 | 4/2012 | Wong et al. | |
| 2012/0095287 A1 | 4/2012 | Wong et al. | |

(Continued)

FOREIGN PATENT DOCUMENTS

| EP | 3150693 A1 | 4/2017 |
| EP | 3305884 A1 | 4/2018 |

(Continued)

OTHER PUBLICATIONS

International Search Report dated Sep. 4, 2018 received in PCT/JP2018/021816.

(Continued)

*Primary Examiner* — Md K Talukder
(74) *Attorney, Agent, or Firm* — Scully, Scott, Murphy & Presser, P.C.

(57) ABSTRACT

An image processing device includes a cell analyzer that analyzes an image of cells cultured within a culture container and that acquires the number of cell divisions experienced by each cell in the image, and also includes a statistical analyzer that calculates a statistical value indicating differentiation potency of each cell in the image from the number of cell divisions acquired by the cell analyzer. The statistical analyzer creates a frequency distribution of the number of cell divisions, and the statistical value represents a bias in the frequency distribution.

17 Claims, 28 Drawing Sheets

(56) References Cited

U.S. PATENT DOCUMENTS

| | | | |
|---|---|---|---|
| 2013/0162795 | A1 | 6/2013 | Wong et al. |
| 2013/0165745 | A1 | 6/2013 | Wong et al. |
| 2013/0217061 | A1 | 8/2013 | Sato et al. |
| 2013/0288293 | A1* | 10/2013 | Sato .................. G01N 33/5011 435/32 |
| 2015/0086102 | A1 | 3/2015 | Fujimoto et al. |
| 2015/0125890 | A1 | 5/2015 | Wong et al. |
| 2015/0160117 | A1 | 6/2015 | Wong et al. |
| 2015/0219632 | A1 | 8/2015 | Sato et al. |
| 2016/0161464 | A1 | 6/2016 | Tsujimoto |
| 2017/0073630 | A1 | 3/2017 | Matsubara |
| 2017/0089820 | A1 | 3/2017 | Wong et al. |
| 2017/0159004 | A1* | 6/2017 | Senda ..................... G01N 21/17 |
| 2018/0040120 | A1* | 2/2018 | Faelan ..................... G06T 11/60 |
| 2018/0314876 | A1* | 11/2018 | Rubin ..................... G06V 20/69 |
| 2019/0095692 | A1 | 3/2019 | Nakatomi et al. |
| 2019/0236784 | A1* | 8/2019 | Bise ..................... G06V 20/698 |
| 2021/0142474 | A1* | 5/2021 | Nakatomi ............... C12M 41/36 |
| 2023/0154003 | A1* | 5/2023 | Taniguchi ............... C12M 41/46 382/133 |

FOREIGN PATENT DOCUMENTS

| | | |
|---|---|---|
| JP | H02-171866 A | 7/1990 |
| JP | 2003-116530 A | 4/2003 |
| JP | 2009-044974 A | 3/2009 |
| JP | 2013-039113 A | 2/2013 |
| JP | 2013-230145 A | 11/2013 |
| JP | 2014-502146 A | 1/2014 |
| JP | 2015-039342 A | 3/2015 |
| JP | 2015-065812 A | 4/2015 |
| JP | 2015-223174 A | 12/2015 |
| JP | 2016-104018 A | 6/2016 |
| JP | 2016-165274 A | 9/2016 |
| JP | 2016-182142 A | 10/2016 |
| JP | 2017-023055 A | 2/2017 |
| JP | 2019-058156 A | 4/2019 |
| WO | 2011/025736 A1 | 3/2011 |
| WO | 2012/056345 A1 | 5/2012 |

OTHER PUBLICATIONS

Surdo, et al., "Quantitative Approaches to Detect Donor and Passage Differences in Adipogenic Potential and Clonogenicity in Human Bone Marrow-Derived Mesenchymal Stem Cells", Tissue Engineering Part C Methods, Nov. 2012, 18(11), pp. 877-889.

Kanade, et al., "Cell Image Analysis: Algorithms, System and Applications", IEEE Workshop on Applications of Computer Vision (WACV), 2011.

Cell growth analysis kit by flow cytometry, CFSE Cell Division Assay Kit, Funakoshi Co., Ltd., Retrieved from the Internet, URL: https://www.funakoshi.co.jp/contents/4276.

\* cited by examiner

FIG. 5

| IDENTIFIER | START TIME | STOP TIME | OPERATOR |
|---|---|---|---|
| CULTURE X | 2018/01/21 11:15 | 2018/01/30 20:15 | A |
| CULTURE Y | 2018/02/22 09:54 | 2018/03/01 16:34 | B |
| CULTURE X | 2018/03/04 11:24 | | C |

FIG. 8

FIRST IMAGING
TIME 2018/1/21 11:15:34

| CELL ID | PARENT CELL ID | POSITION | NUMBER OF CELL DIVISIONS | STATUS |
|---|---|---|---|---|
| 0 | – | (10, 10)–(25, 30) | 0 | ALIVE |
| 1 | – | (12, 190)–(30, 208) | 0 | ALIVE |
| 2 | – | (332, 99)–(345, 120) | 0 | ALIVE |
| 3 | – | (988, 450)–(1024, 480) | 0 | ALIVE |
| ... | | | | |

SECOND IMAGING
TIME 2018/1/21 11:30:34

| CELL ID | PARENT CELL ID | POSITION | NUMBER OF CELL DIVISIONS | STATUS |
|---|---|---|---|---|
| 0 | – | (12, 18)–(28, 40) | 0 | ALIVE |
| 1 | – | (12, 188)–(30, 206) | 0 | ALIVE |
| 2 | – | (334, 101)–(348, 125) | 0 | UNDERGOING CELL DIVISION |
| 3 | – | (980, 450)–(1015, 482) | 0 | ALIVE |
| ... | | | | |

⋮

N-TH IMAGING
TIME 2018/1/22 23:30:34

| CELL ID | PARENT CELL ID | POSITION | NUMBER OF CELL DIVISIONS | STATUS |
|---|---|---|---|---|
| 0 | – | | 0 | DEAD |
| 1 | – | (12, 188)–(30, 206) | 0 | ALIVE |
| 2 | – | (334, 101)–(348, 125) | 0 | DIVIDE→ID4, ID5 |
| 3 | – | (980, 450)–(1015, 482) | 0 | ALIVE |
| 4 | 2 | (453, 180)–(480, 200) | 1 | ALIVE |
| 5 | 2 | (283, 152)–(300, 179) | 1 | ALIVE |

FIG. 9

| NUMBER OF CELL DIVISIONS | NUMBER OF CELLS |
|---|---|
| NONE | 20 CELLS |
| ONCE | 15 CELLS |
| TWICE | 15 CELLS |
| THREE TIMES | 10 CELLS |
| FOUR TIMES | 10 CELLS |

FIG. 26

| IDENTIFIER | START TIME | STOP TIME | OPERATOR | EVALUATION REULT |
|---|---|---|---|---|
| CULTURE X | 2018/01/21 11:15 | 2018/01/30 20:15 | A | GOOD |
| CULTURE Y | 2018/02/22 09:54 | 2018/03/01 16:34 | B | POOR |
| CULTURE Z | 2018/03/04 11:24 | | C | |

IMAGE PROCESSING DEVICE AND CULTURE EVALUATION SYSTEM

CROSS-REFERENCE TO RELATED APPLICATIONS

This is a continuation of International Application PCT/JP2018/021816, with an international filing date of Jun. 7, 2018, which is hereby incorporated by reference herein in its entirety.

TECHNICAL FIELD

The present invention relates to image processing devices and culture evaluation systems.

BACKGROUND ART

In the field of regenerative medicine in the related art, various types of cells have been used in research. Mesenchymal stem cells (MSCs) have an ability to differentiate into bones, cartilage, and fat and have been actively researched. Normally, a researcher ensures the number of cells required for an experiment by increasing the number of purchased MSCs by culturing, and subsequently causes the MSCs to differentiate into target cells. In general, since cell culturing is unstable, techniques for ascertaining the culture status have been proposed (e.g., see PTL 1).

On the other hand, it is reported that there is a correlation between a colony forming unit (CFU) and the differentiation potency of MSCs (e.g., see Non Patent Literature 1). A CFU is the percentage of the number of colonies formed after two to three weeks from the timing when cells are seeded at an extremely low density. According to NPL 1, the CFU increases with higher differentiation potency of MSCs. Therefore, the differentiation potency of MSCs can be predicted by measuring the CFU.

CITATION LIST

Patent Literature

{PTL 1}
Japanese Unexamined Patent Application, Publication No. 2017-23055

Non Patent Literature

{NPL 1}
Jessica Lo Surdo, et al., "Quantitative Approaches to Detect Donor and Passage Differences in Adipogenic Potential and Clonogenicity in Human Bone Marrow-Derived Mesenchymal Stem Cells", Tissue Engineering Part C: Methods, Nov. 2012, 18(11), pp. 877-889.

SUMMARY OF INVENTION

An aspect of the present invention provides an image processing device including a processor configured to analyze an image of cells cultured within a culture container and acquire the number of cell divisions experienced by each cell in the image, and calculate a statistical value indicating differentiation potency of each cell in the image from the number of cell divisions acquired by analyzing the image, wherein the processor creates a frequency distribution of the number of cell divisions, and the statistical value represents a bias in the frequency distribution.

BRIEF DESCRIPTION OF DRAWINGS

FIG. 5 illustrates an example of a database stored in a storage.

FIG. 8 illustrates an example of cell analysis data generated by the cell analyzer.

FIG. 9 is a table illustrating an example of an analysis result obtained by a statistical analyzer and indicating the number of cells corresponding to each number of cell divisions.

FIG. 26 illustrates an example of a database stored in the storage of the culture evaluation system in FIG. 25.

DESCRIPTION OF EMBODIMENTS

First Embodiment

A culture evaluation system according to a first embodiment of the present invention will be described with reference to the drawings.

Figure 1:
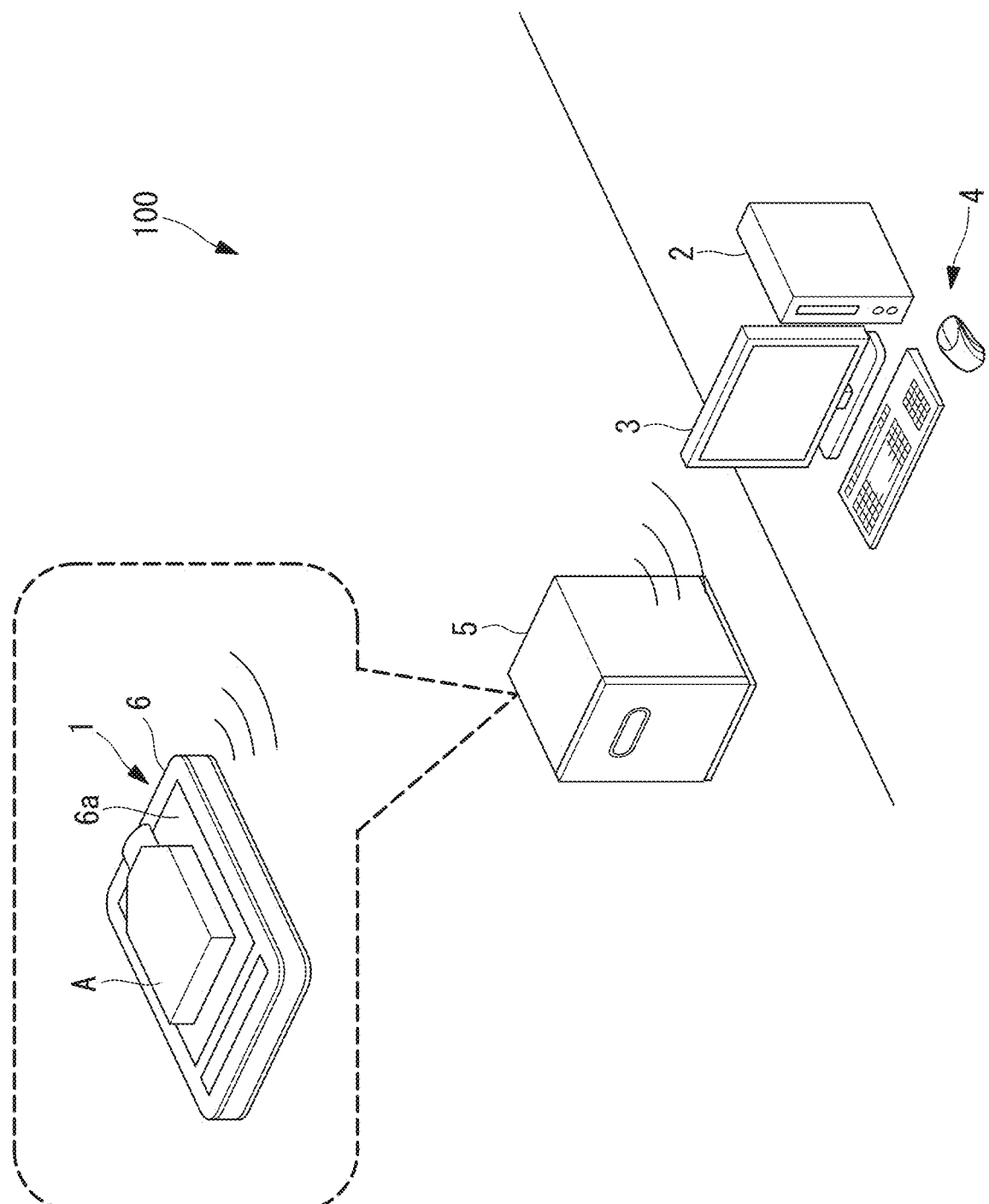
FIG. 1 is an external view illustrating the overall configuration of a culture evaluation system according to a first embodiment of the present invention.

As shown in FIG. 1, a culture evaluation system 100 according to this embodiment includes a culture observation device (image sensor) 1 that acquires an image of cells B within a culture container A, a personal computer (PC) 2 that processes the image acquired by the culture observation device 1, and a display 3 that displays, for example, the image acquired by the culture observation device 1 and a processing result obtained by the PC 2. Reference sign 5 denotes an incubator.

Figure 2:
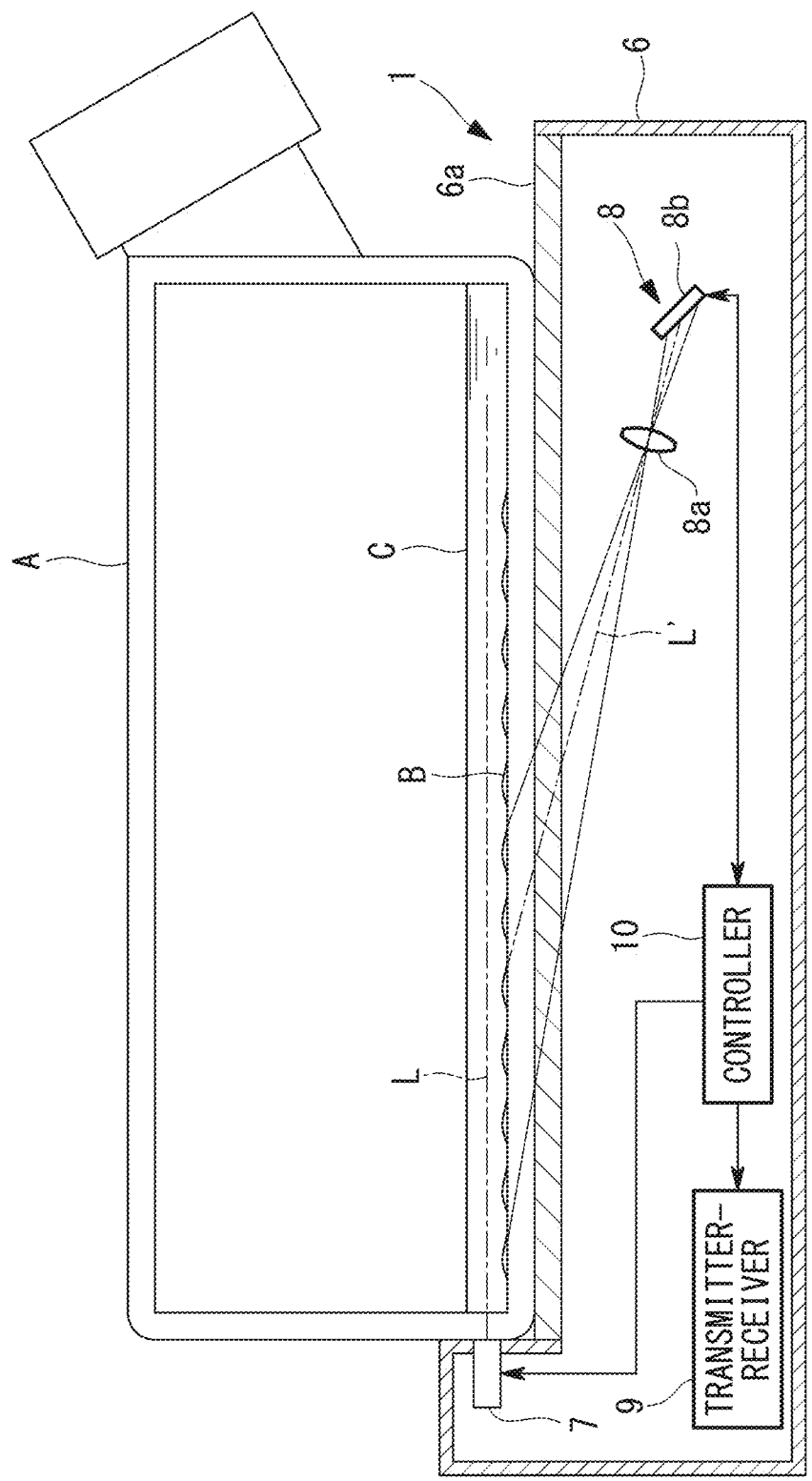
FIG. 2 is a vertical sectional view illustrating the configuration of a culture observation device in the culture evaluation system in FIG. 1.

FIG. 2 illustrates an example of the culture observation device 1. As shown in FIG. 2, the culture observation device 1 includes a box-shaped base 6 on which the culture container A is mounted, a light source 7 provided in the base 6, an imaging unit 8, a transmitter-receiver 9, and a controller 10.

The culture container A is, for example, a flask used for culturing cells and is composed of an optically transparent material.

An upper plate 6a of the base 6 is a flat component composed of a transparent material and is used as a stage on which the culture container A is placed.

The light source 7 emits illumination light L toward the culture container A on the stage 6a so as to illuminate the cells B within the culture container A with the illumination light L. For example, the light source 7 is disposed at a position higher than the stage 6a and emits the illumination light L in a direction parallel to the stage 6a.

The imaging unit 8 acquires an image of the cells B within the culture container A via the stage 6a. For example, the imaging unit 8 includes a focusing lens 8a that collects illumination light L' scattered in the cells B to form an image of the cells B, and an imaging element 8b that acquires the image of the cells B formed by the focusing lens 8a. The base 6 is provided with a moving mechanism (not shown) therein, such as a linear actuator, for moving the imaging unit 8 in the direction parallel to the stage 6a. An imaging position where the imaging unit 8 acquires an image can be changed by actuating the moving mechanism.

The transmitter-receiver 9 exchanges data and signals with the PC 2 disposed outside the incubator 5 by using wireless communication. The image acquired by the imaging unit 8 is transmitted to the PC 2 via the transmitter-receiver 9.

The controller 10 receives a control signal from the PC 2 via the transmitter-receiver 9 and controls the light source 7 and the imaging unit 8 in accordance with the control signal. For example, the controller 10 is equipped with a timer (not shown) that measures time, and controls the light source 7 and the imaging unit 8 such that an image is acquired at an imaging time point and imaging position set by an operator.

Figure 3:
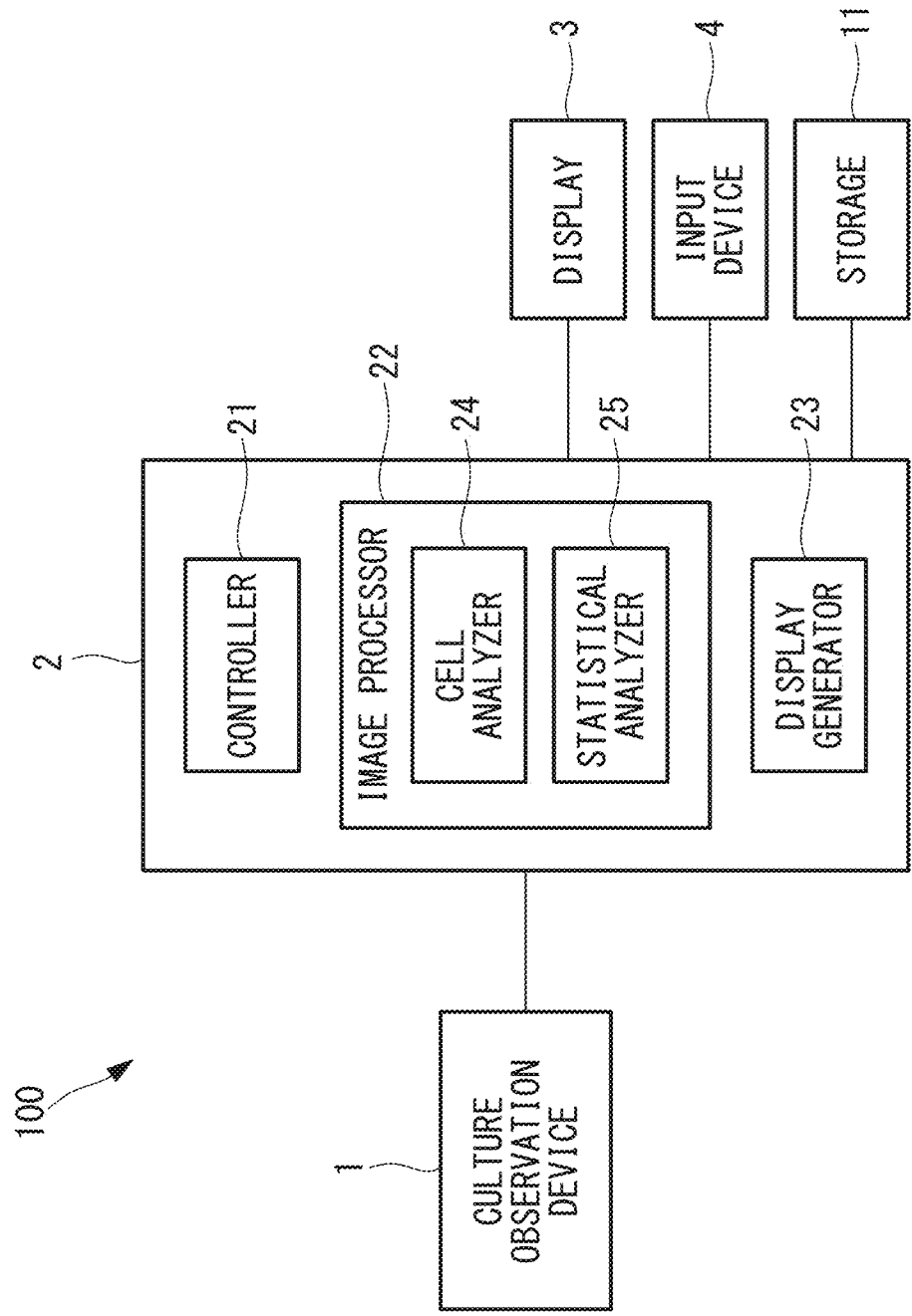
FIG. 3 is a block diagram illustrating the overall configuration of the culture evaluation system in FIG. 1.

As shown in FIG. 3, the PC 2 is connected to the display 3, an input device 4, and a storage 11.

The display 3 is a display device, such as a liquid crystal monitor. The display 3 displays display data received from the PC 2.

The input device 4 is, for example, a keyboard or a mouse.

The storage 11 is, for example, a storage device externally connected to the PC 2. The storage 11 may alternatively be a storage device contained in the PC 2.

The PC 2 includes a controller 21 that controls the culture observation device 1, an image processor (image processing device) 22 that processes an image acquired by the culture observation device 1, and a display generator 23 that generates display data of a processing result obtained by the image processor 22. The controller 21, the image processor 22, and the display generator 23 are realized by software installed in the PC 2 and programmed to cause a central processing unit (CPU) to execute a process to be described below.

Figure 4:
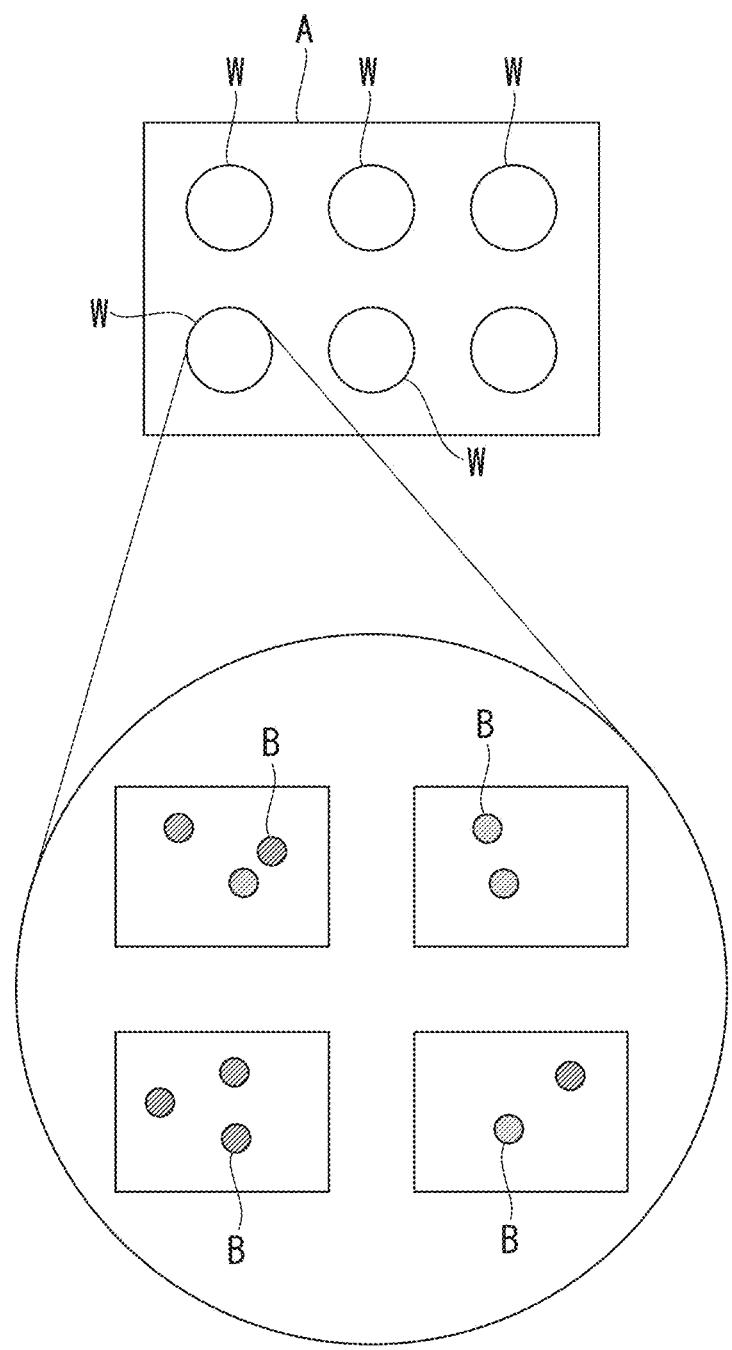
FIG. 4 illustrates an imaging position when a multi-well plate is used.

The controller 21 transmits a control signal to the culture observation device 1 to cause the culture observation device 1 to execute an imaging process at a preset imaging time point at a preset imaging position. The imaging time point and the imaging position are set by the operator using the input device 4. In order to periodically acquire an image of the cells B within a culturing period and to sequentially evaluate the status of the cells B, the imaging time point is set to intervals of a fixed time period (e.g., 15 minutes). Thus, time-series images are transmitted from the culture observation device 1 to the PC 2 at fixed time intervals. As shown in FIG. 4, a plurality of imaging positions may be set, and the imaging unit 8 may be caused to acquire images of the plurality of imaging positions within the culture container A at each imaging time point. The culture container A shown in FIG. 4 is a multi-well plate having a plurality of wells W.

The image processor 22 includes a cell analyzer 24 and a statistical analyzer 25. An image transmitted from the culture observation device 1 to the PC 2 is stored in the storage 11 and is also input to the cell analyzer 24 in the image processor 22.

FIG. 5 illustrates an example of a database stored in the storage 11. The storage 11 receives an analysis result, to be described below, obtained by each of the cell analyzer 24 and the statistical analyzer 25 from the image processor 22 and stores an image and the analysis result in a time-series fashion in association with a culture identifier and the imaging time point. Consequently, a database in which the culture identifier, the imaging start time, the imaging position, the imaging time point, and the analysis result which are associated with one another is created in the storage 11. Every time a culturing process is performed, culturing-related information is added to the database. Therefore, past and current culturing-related analysis results are accumulated in the database of the storage 11. The database may also have operators and culturing conditions stored therein. Examples of the culturing conditions include the cell type, the temperature and the carbon dioxide level in the incubator 5, the type of a culture medium, and the type of the culture container A.

Figure 6A:
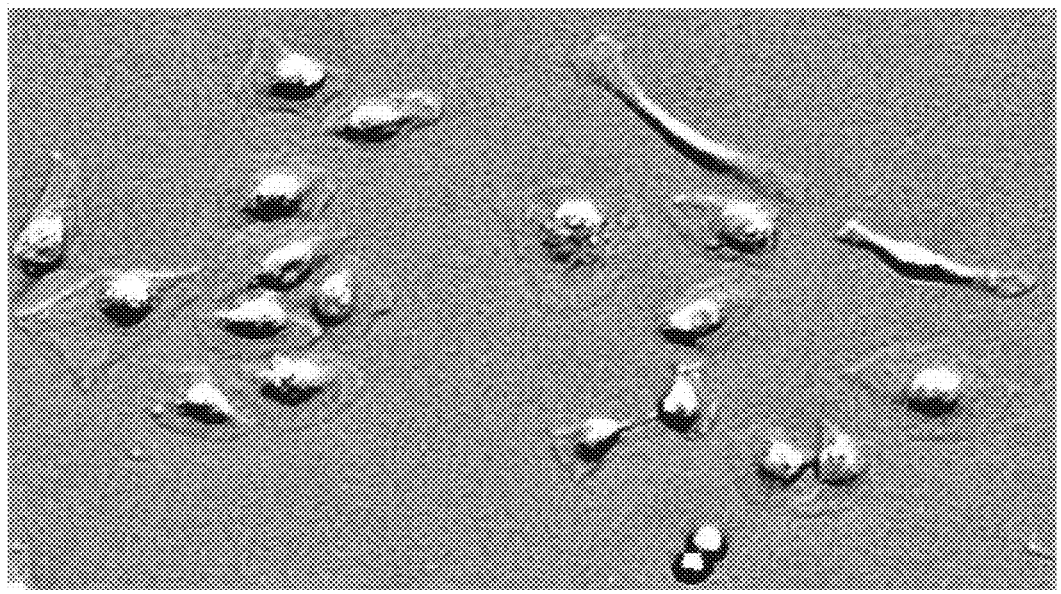
FIG. 6A illustrates an example of an image of cells within a culture container, acquired by the culture observation device.
Figure 6B:
FIG. 6B illustrates an example of an analysis result of the image in FIG. 6A, obtained by a cell analyzer.

The cell analyzer 24 analyzes an image to detect each cell in the image and to acquire the number of cell divisions experienced by each cell B. FIG. 6A illustrates an example of an image acquired by the culture observation device 1. FIG. 6B illustrates an example of a detection result of the cells B in the image in FIG. 6A and an analysis result of the number of cell divisions.

The method used for counting the number of cell divisions is described in Reference Literature 1 (Takeo Kanade et al., "Cell Image Analysis: Algorithms, System and Applications", IEEE Workshop on Applications of Computer Vision (WACV), 2011). Every time the cell analyzer 24 receives a new image, the cell analyzer 24 detects the cells B and the positions thereof in the new image. Then, the cell analyzer 24 compares the cells B in the new image with the cells B in the preceding image to track the individual cells B, thereby determining the number of cell divisions experienced by each cell B.

Figure 7:
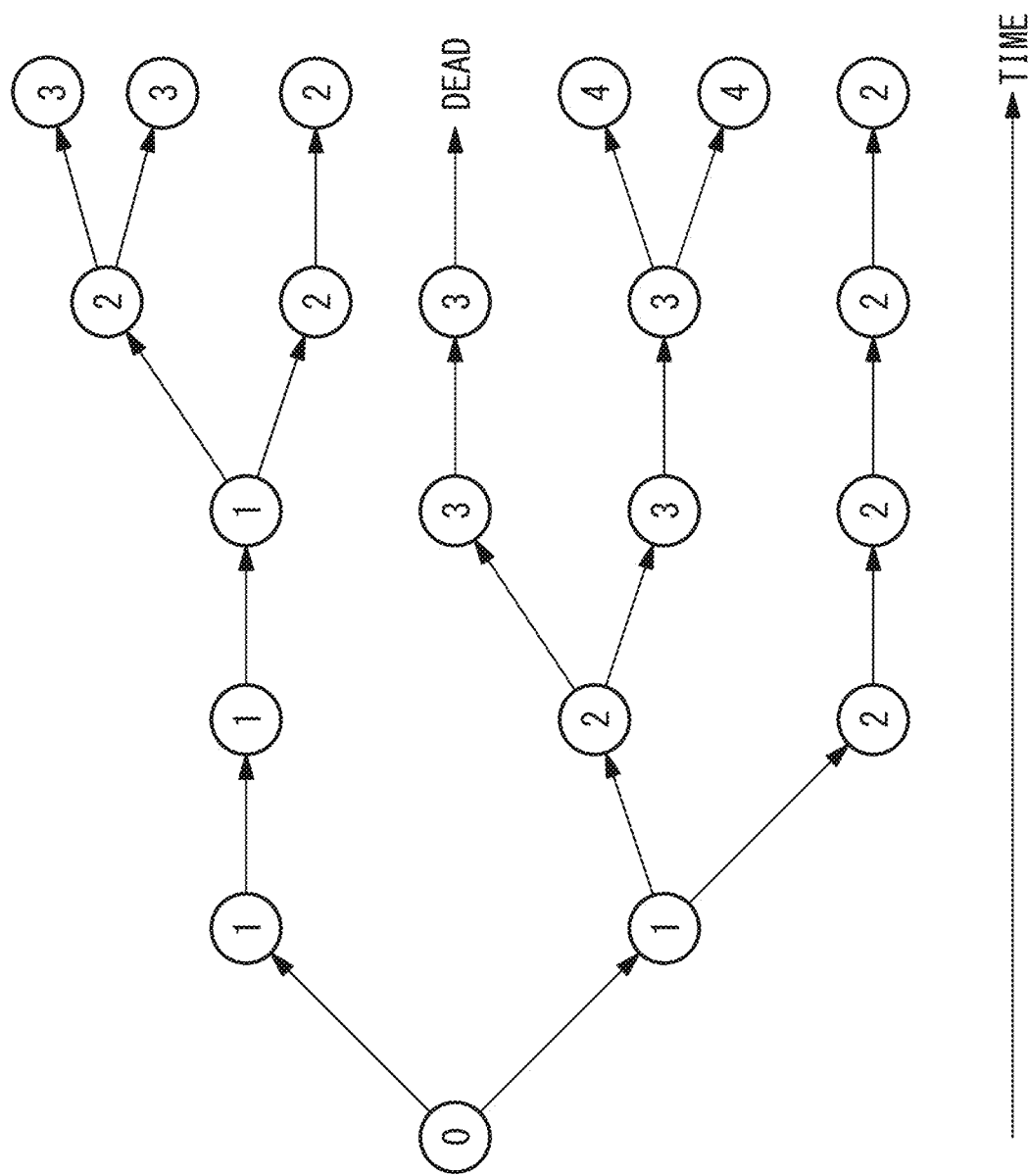
FIG. 7 illustrates the process of cell division of a single cell.

FIG. 7 illustrates a process of how a single cell B increases in number as a result of cell division. Each circle denotes a single cell, and numerical values in the circles denote the number of cell divisions. As shown in FIG. 7, the cell analyzer 24 sets the number of cell divisions experienced by each cell B in a first input image to zero. A cell B that has undergone k cell divisions divides into two cells having undergone (k+1) cell divisions.

FIG. 8 illustrates an example of an analysis result obtained by the cell analyzer 24. The cell analyzer 24 adds a cell identifier (ID) to each cell in the first input image. When a cell undergoes cell division, the mother cell is given a parent cell ID, and the two daughter cells produced as a result of the cell division are individually given new cell IDs. Therefore, at the start of a culturing process, the field for the parent cell ID is blank. The position of each cell is recorded using the coordinates of the upper left corner and the lower right corner of the cell, with the upper left corner of the image being defined as an origin. The position of each cell may alternatively be the center of the cell. The cell analyzer 24 generates cell analysis data in which the cell ID, the position, and the number of cell divisions are associated with one another. The cell analyzer 24 may further store the status of each cell therein (e.g., alive, dead, or undergoing cell division). The cell analyzer 24 associates the cell analysis data obtained from the image with the imaging time point of the image and transmits the cell analysis data to the statistical analyzer 25. Moreover, the cell analysis data is stored in the storage 11.

The statistical analyzer 25 performs a statistical analysis on the cell analysis data received from the cell analyzer 24 so as to calculate a statistical value indicating the differentiation potency of each cell B within the culture container A. In detail, as shown in FIG. 9, the statistical analyzer 25 counts the number of cells corresponding to each number of cell divisions contained in the cell analysis data. Accordingly, the number of cells corresponding to each number of cell divisions existing in the image is calculated. Then, the statistical analyzer 25 creates a cell-division frequency histogram (frequency distribution). In the histogram, the abscissa axis denotes the number of cell divisions, whereas the ordinate axis denotes the number of cells.

Figure 10:
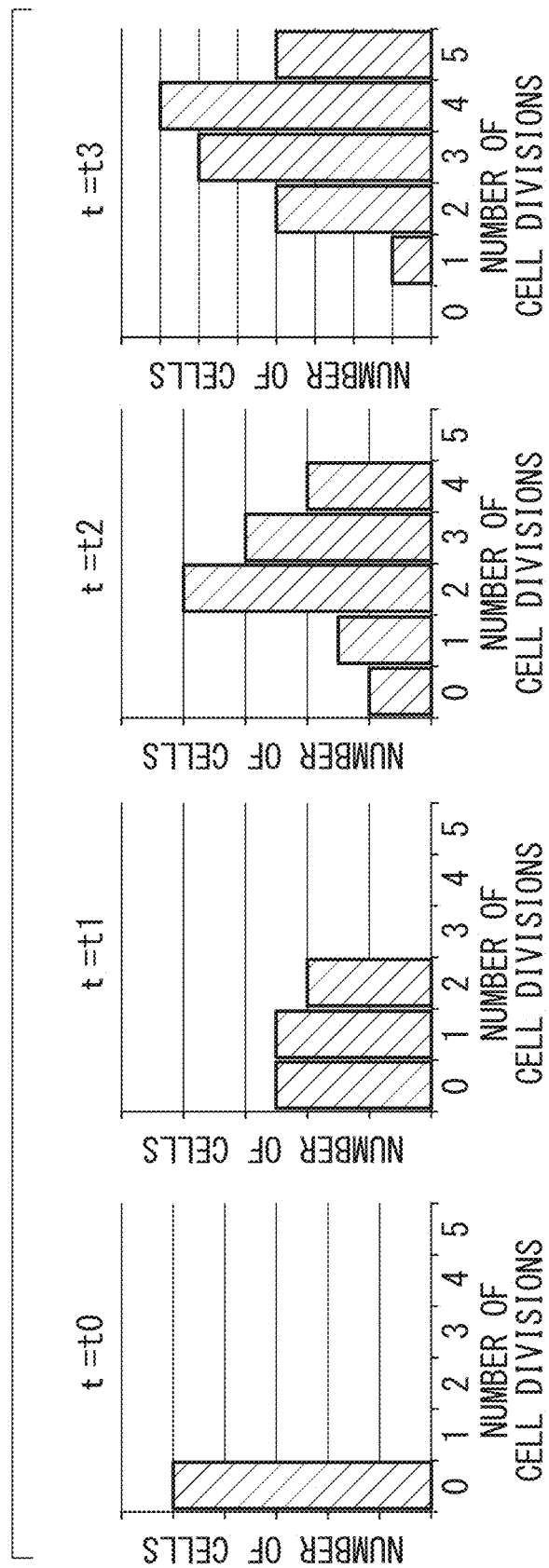
FIG. 10 illustrates cell-division frequency histograms for a plurality of imaging time points.

FIG. 10 illustrates cell-division frequency histograms for a plurality of imaging time points t=t0, t1, t2, and t3 (t0<t1<t2<t3). As shown in FIG. 10, the number of cells having experienced a small number of cell divisions decreases with time, whereas the number of cells having experienced a large number of cell divisions increases with time.

Figure 11A:
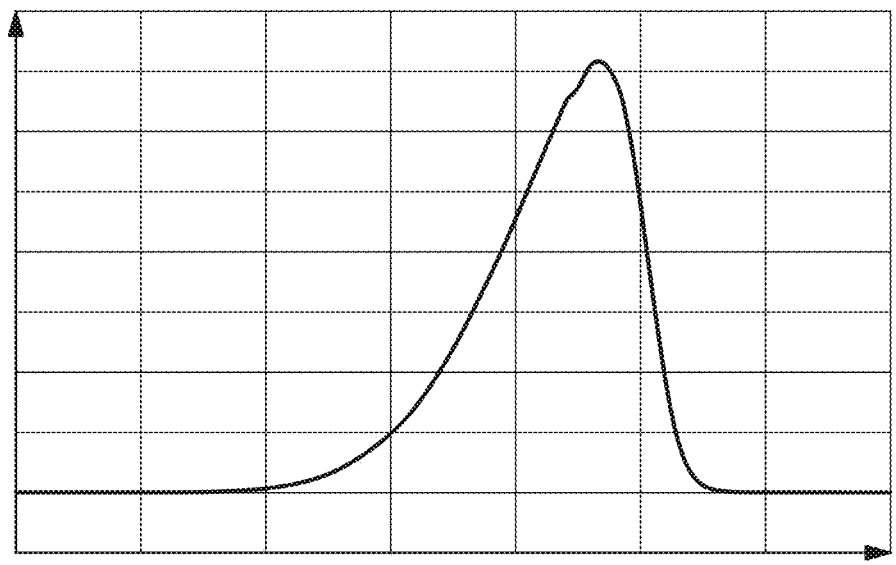
FIG. 11A illustrates an example of a distribution having a negative skewness.
Figure 11B:
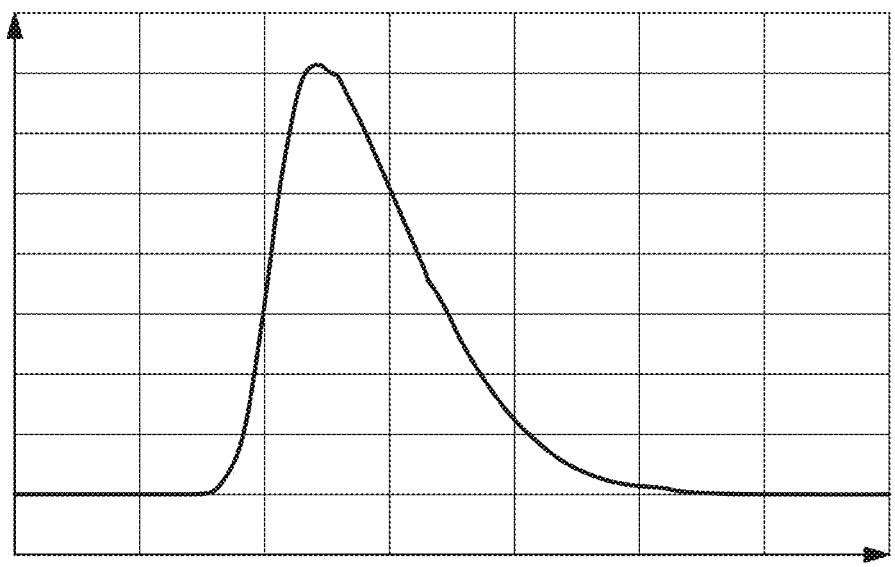
FIG. 11B illustrates an example of a distribution having a positive skewness.

Subsequently, the statistical analyzer 25 calculates the skewness in each histogram. The skewness is a statistical value indicating a bias in a distribution and expresses asymmetry in the distribution. A symmetrical distribution (e.g., a normal distribution) has zero skewness. As shown in FIG. 11A, a distribution biased to the right (i.e., the side with the higher number of cell divisions) has a negative skewness. As shown in FIG. 11B, a distribution biased to the left (i.e., the side with the smaller number of cell divisions) has a positive skewness. Therefore, a negative skewness indicates that there is a large number of cells having experienced a large number of cell divisions, whereas a positive skewness indicates that there is a large number of cells having experienced a small number of cell divisions.

The skewness is calculated in accordance with the following procedure.

First, an average number $\mu$ of cell divisions, a variance $\sigma^2$, and a standard deviation $\sigma$ are calculated in accordance with Expressions (1), (2), and (3) indicated below. In this case, k (k=0, 1, 2, . . . , $k_{max}$) indicates the number of cell divisions, and $k_{max}$ indicates a maximum value of the number of cell divisions at a certain imaging time point. The number k of cell divisions experienced by all cells at the start of an imaging process is zero. Nk (Nk=N0, N1, N2, . . . , $Nk_{max}$) indicates the number of cells that have undergone k cell divisions, and N indicates the total number of cells (i.e., N=N0+N1+N2+ . . . +$Nk_{max}$).

{Expression 1}

$$\mu = \frac{\sum_{k=0}^{k_{max}} k N_k}{N} \quad (1)$$

{Expression 2}

$$\sigma^2 = \frac{\sum_{k=0}^{k_{max}} (k-\mu)^2 N_k}{N} \quad (2)$$

{Expression 3}

$$\sigma = \sqrt{\sigma^2} \quad (3)$$

Subsequently, a skewness Skew is calculated in accordance with Expression (4) indicated below.

{Expression 4}

$$\text{Skew} = \frac{\sum_{k=0}^{k_{max}} (k-\mu)^3 N_k}{N\sigma^3} \quad (4)$$

The variance $\sigma^2$ may be an unbiased variance defined by Expression (2') indicated below, and the skewness Skew may be an unbiased skewness defined by Expression (4') indicated below.

{Expression 5}

$$\sigma^2 = \frac{\sum_{k=0}^{k_{max}} (k-\mu)^2 N_k}{N-1} \quad (2')$$

{Expression 6}

$$\text{Skew} = \frac{N}{(N-1)(N-2)} \frac{\sum_{k=0}^{k_{max}} (k-\mu)^3 N_k}{\sigma^3} \quad (4')$$

The display generator 23 generates numerical display of the skewness received from the statistical analyzer 25 and transmits the numerical display to the display 3 where the numerical display is displayed.

Figure 12:
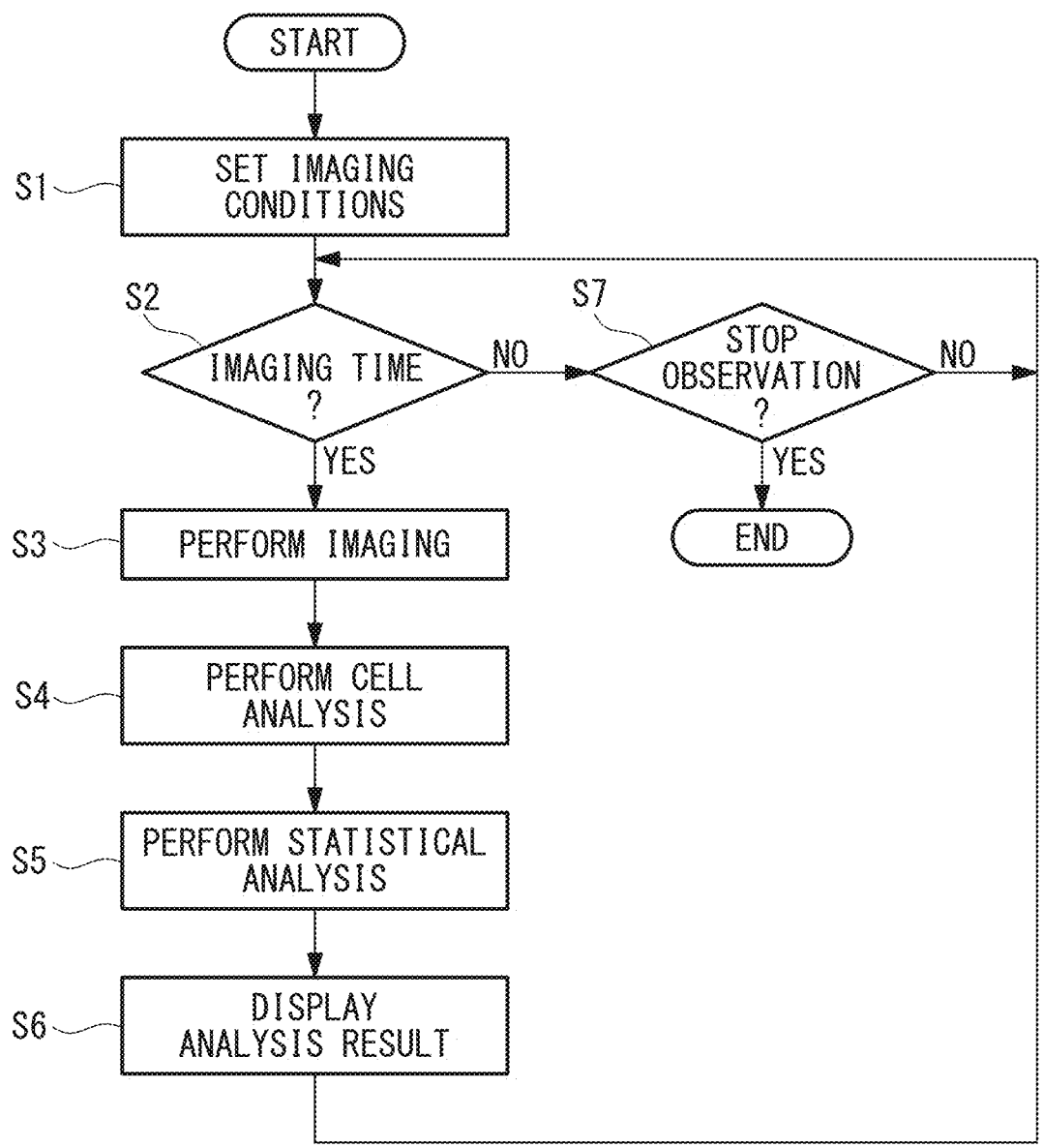
FIG. 12 is a flowchart illustrating the operation of the culture evaluation system in FIG. 1.

Next, the operation of the culture evaluation system 100 having the above-described configuration will be described with reference to FIG. 12.

In order to evaluate the culture status of the cells B by using the culture evaluation system 100 according to this embodiment, the culture container A containing the cells B and a culture medium C is placed on the stage 6a, the culture observation device 1 is disposed in the incubator 5 together with the culture container A, and the cells B are cultured within the culture container A in an environment where the temperature and humidity in the incubator 5 are controled.

After the culturing process commences, the operator sets the imaging time point and the imaging position by using the input device 4 (step S1). The controller 21 generates a control signal based on the set imaging time point and the set imaging position and transmits the control signal to the culture observation device 1. The controller 10 of the culture observation device 1 actuates the light source 7 at the set imaging time point so as to cause the imaging element 8b to execute an imaging process (step S2 and step S3). An image acquired by the imaging element 8b is transmitted to the PC 2 from the culture observation device 1. The image is stored in the storage 11 and is also processed by the image processor 22 in the PC 2.

The image processor 22 causes the cell analyzer 24 to execute an image analysis (step S4) and also causes the statistical analyzer 25 to execute a statistical analysis (step S5).

In detail, the cell analyzer 24 detects the individual cells B in the image. If the image to be analyzed is an image from the first imaging time point, the calculated number of cell divisions experienced by each cell B is zero. If the image to be analyzed is an image from the second imaging time point or onward, the number of cell divisions experienced by each cell B is calculated based on a comparison with an image or images acquired up to that time.

Then, the statistical analyzer 25 creates a histogram indicating the number of cells corresponding to each number of cell divisions, and calculates the skewness in the histogram.

Subsequently, the display generator 23 generates numerical display of the skewness value. The generated numerical display is transmitted to the display 3 and is displayed on the display 3 (step S6). The operator evaluates the culture status of the cells B currently being cultured in the culture container A based on the numerical value of the skewness displayed on the display 3.

When the cells B within the culture container A have experienced satisfactory cell division overall, the shape of the histogram is close to a symmetrical shape, as in a normal distribution, or is biased toward the side with the larger number of cell divisions, so that the skewness becomes zero or a negative value. On the other hand, if some of the cells B within the culture container A have not experienced cell division, the shape of the histogram is biased toward the side with the smaller number of cell divisions, so that the skewness becomes a positive value. Therefore, based on the skewness in the cell-division frequency histogram, it can be determined whether the cells B within the culture container A are repeatedly undergoing satisfactory cell divisions overall or whether the culture container A contains cells B that have not experienced cell division.

The fact that the number of cell divisions experienced by each cell B is large is equivalent to the fact that the colony forming unit (CFU) is large, thus meaning that the differentiation potency of each cell B is predicted as being high. In contrast, the fact that the number of cell divisions experienced by each cell B is small is equivalent to the fact that the CFU is small, thus meaning that the differentiation potency of each cell B is predicted as being low. Therefore, similar to a CFU assay, the operator can readily evaluate the differentiation potency of the cells B being cultured based on the value of the skewness displayed on the display 3. Moreover, the operator can evaluate the differentiation potency of the cells B prior to an experiment and only use cells B having certain differentiation potency for the experiment, so that an experiment with high reproducibility can be performed.

Calculation of the skewness only needs acquisition and analysis of images of the cells B currently being cultured. Specifically, it is not necessary to prepare cells for evaluating the differentiation potency separately from the cells B within the culture container A or to perform a differentiation-potency evaluation test by using the cells B. Accordingly, the differentiation potency of the cells B being cultured can be quickly evaluated by a simple method.

In addition to the numerical display of the skewness, the display 3 may display the cell-division frequency histogram. Based on the histogram, the operator can ascertain the cell-division status of the cells within the culture container A in more detail. For example, the operator can ascertain, from the histogram, whether the overall number of cell divisions is large or small, whether there is a cell that has experienced an unusually large number of cell divisions, or whether there is a cell that has not experienced cell division at all.

Figure 13:
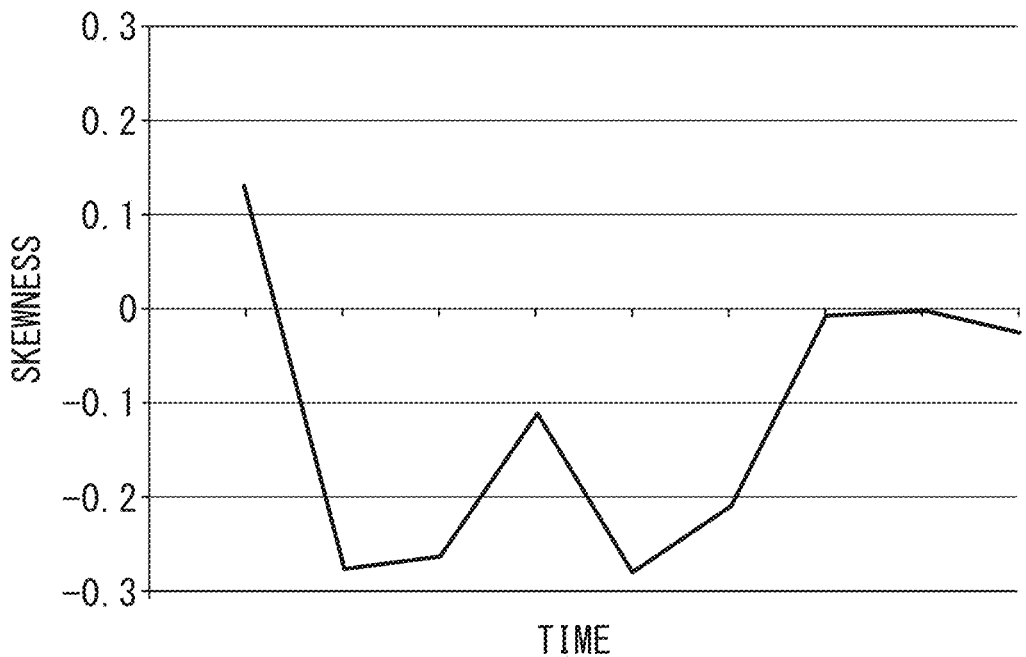
FIG. 13 illustrates an example of a graph indicating a temporal change in the skewness of a cell-division frequency histogram.

Furthermore, as shown in FIG. 13, in place of or in addition to the numerical display of the skewness, the display 3 may display a graph indicating a temporal change in the skewness calculated up to that point.

Figure 14A:
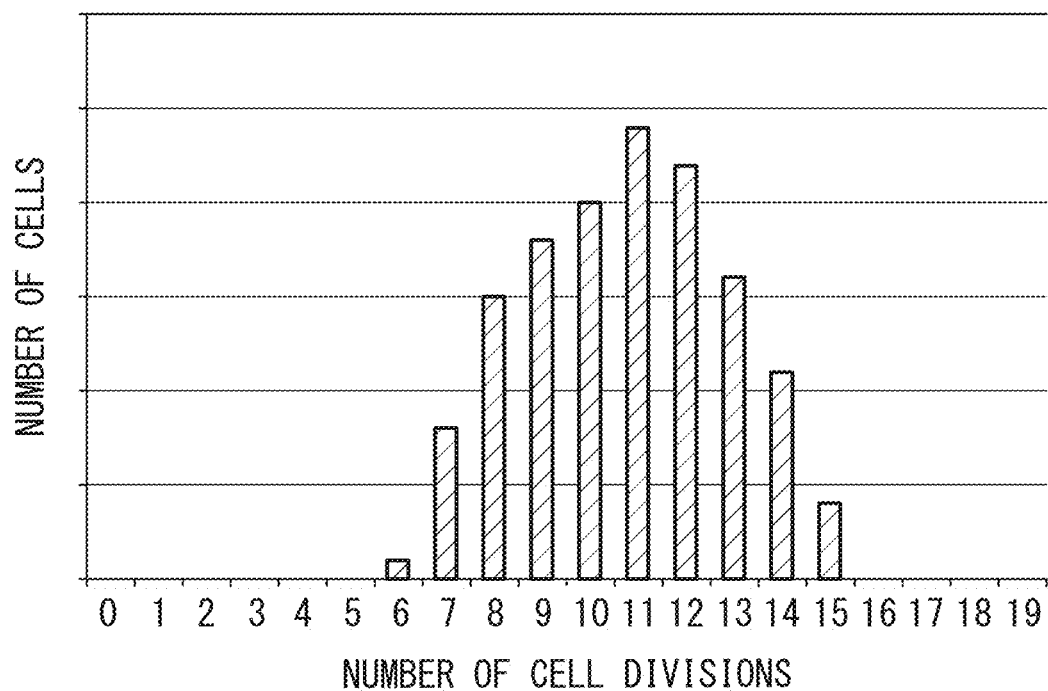
FIG. 14A illustrates an example of a histogram in which the number of cells corresponding to each number of cell divisions is defined as a frequency.
Figure 14B:
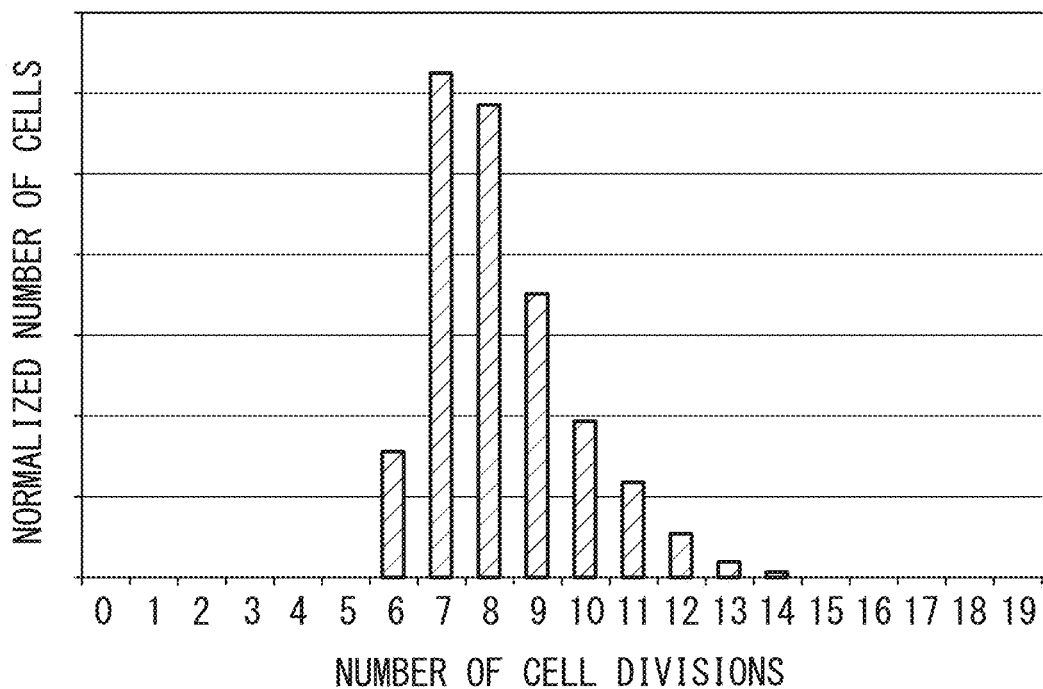
FIG. 14B illustrates an example of a histogram that is created from the histogram in FIG. 14A and in which the number of cells at the start of a culturing process is defined as a frequency.

In this embodiment, the statistical analyzer 25 creates a histogram in which the number of cells corresponding to each number of cell divisions in an image is defined as a frequency, as shown in FIG. 14A. Alternatively, as shown in FIG. 14B, a normalized histogram in which a normalized number of cells is defined as a frequency may be created.

A normalized number of cells is a numerical value obtained by dividing the number of cells corresponding to k cell divisions by $2^k$. By dividing the number of cells by $2^k$, the number of cells corresponding to k cell divisions is converted into the number of cells at the start of the culturing process.

Because the number of cell divisions increases as the culturing time elapses, the histogram shifts rightward. Thus, two culture histograms with different lengths in the culturing time cannot be simply compared with each other. By normalizing the number of cells, two culture histograms with different lengths in the culturing time can be compared with each other. The calculation of a statistical value from the histogram with the normalized number of cells is performed in a manner similar to the above-described statistical-value calculation.

Instead of dividing the number of cells by $2^k$, a logarithm of the number of cells may be used.

In this embodiment, the statistical analyzer 25 acquires the number of cells corresponding to each number of cell divisions from the entire image and creates a histogram in which the number of cells is defined as a frequency. Alternatively, the image may be divided into a plurality of regions, and a histogram in which the number of regions with representative values for the statistical values in the plurality of regions is defined as a frequency may be created.

Figure 15:
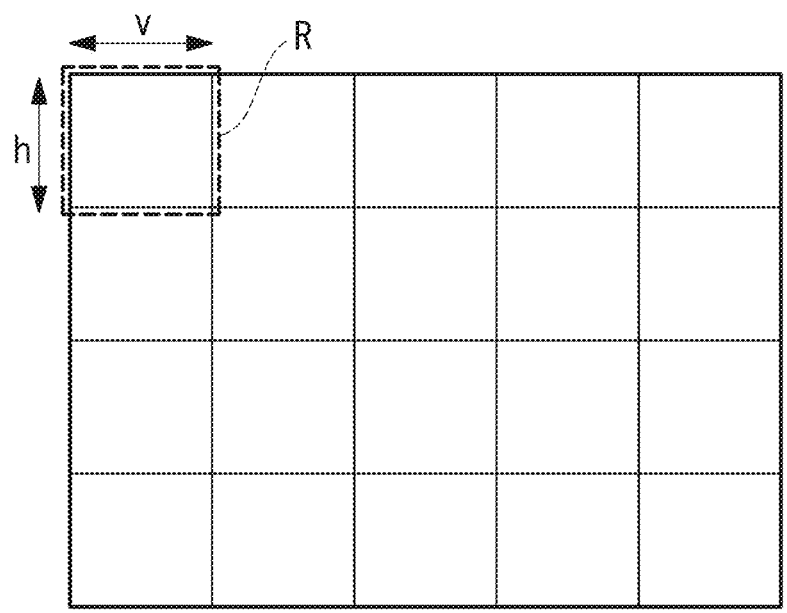
FIG. 15 illustrates a method of dividing an image into a plurality of regions.

In detail, as shown in FIG. 15, the cell analyzer 24 divides the image into (Nh×Nv) regions R. The division number (i.e., the width h and the height v of each region) of the image is set in accordance with the size of each cell B in the image. Then, the cell analyzer 24 acquires the number of cell divisions experienced by the individual cells B within each region R.

Figure 16:
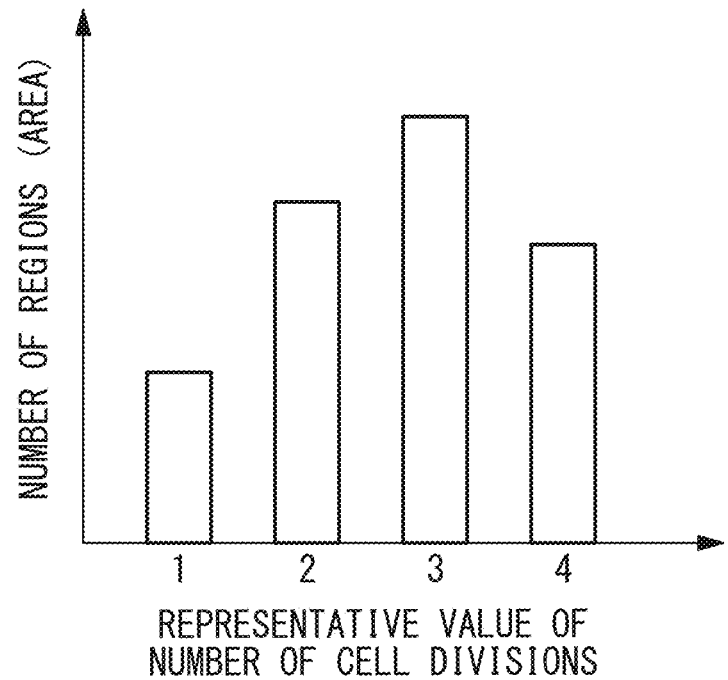
FIG. 16 illustrates an example of a histogram as a modification of a histogram generated by the statistical analyzer and in which the number of regions with representative values for the number of cell divisions is defined as a frequency.

The statistical analyzer 25 calculates a representative value of the number of cell divisions experienced by the cells B within each region R. The representative value is, for example, a maximum value for the number of cell divisions experienced by the cells B within each region R. The representative value may alternatively be an average value of the number of cell divisions experienced by the cells B within each region R. Then, the statistical analyzer 25 counts the number of regions R with the corresponding representative values and creates a histogram indicating the number of regions R with the representative values, as shown in FIG. 16. In the histogram, the abscissa axis denotes a representative value, whereas the ordinate axis denotes the number of regions R. Then, the statistical analyzer 25 calculates the skewness in the histogram of the representative value for the number of cell divisions.

The number of cell divisions experienced by each cell B within the culture container A may sometimes vary spatially due to, for example, uneven density of cells B when being seeded into the culture container A, a difference in the number of cells depending on the location within the culture container A, or local intrusion of a specific type of cells, such as cancer cells. The number of cell divisions may also vary spatially due to intrusion of cells with extremely low or high differentiation potency, as compared with normal cells B, within the culture container A.

When the cells B are undergoing cell division equally within the entire culture container A, a bias in the representative-value distribution is small, thus resulting in a small absolute value of the skewness. In contrast, when the number of cell divisions experienced by each cell is locally large or small, the absolute value of the skewness becomes larger. Thus, it can be determined whether or not there are spatial variations in the differentiation potency of the cells within the culture container A based on the skewness in the histogram in FIG. 16, and it can be evaluated whether the differentiation potency of the cells B is good or not in the entire culture container A.

In this modification, it can also be determined whether there are spatial variations in the differentiation potency of the cells B within the culture container A based on a variance in the histogram. Therefore, the variance in the histogram may be calculated in place of the skewness.

The number of regions on the ordinate axis of the histogram in FIG. 16 is equivalent to an area. Therefore, the percentage of area by which the cells B corresponding to each number of cell divisions occupy the image can be determined from the histogram.

The statistical analyzer 25 may calculate the area that the cells B corresponding to each number of cell divisions occupy the image from the area of each cell B. The area of each cell B (i.e., the number of pixels) is calculated by using, for example, a watershed algorithm.

As an alternative to this embodiment in which the statistical analyzer 25 only calculates the skewness in the histogram, the statistical analyzer 25 may calculate another statistical value in addition to the skewness. Another statistical value is, for example, at least one of an average value, a median value, a mode value, a variance, and a kurtosis. The statistical analyzer 25 may calculate a plurality of types of statistical values, determine a statistical value with a high correlation with the differentiation potency of the cells from among the plurality of types of statistical values by means of a multivariate analysis, and combine the determined statistical value with the skewness.

FIG. 17A to FIG. 18C illustrate examples of combinations of the skewness and the average value.

Figure 17A:
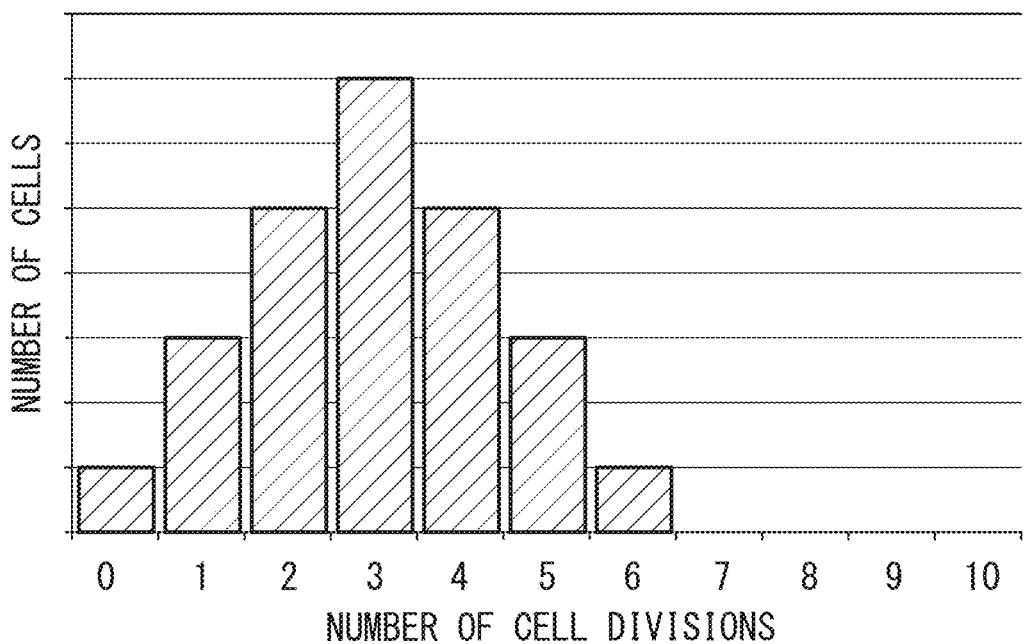
FIG. 17A illustrates an example of a cell-division frequency histogram of a cell group with low differentiation potency.
Figure 17B:
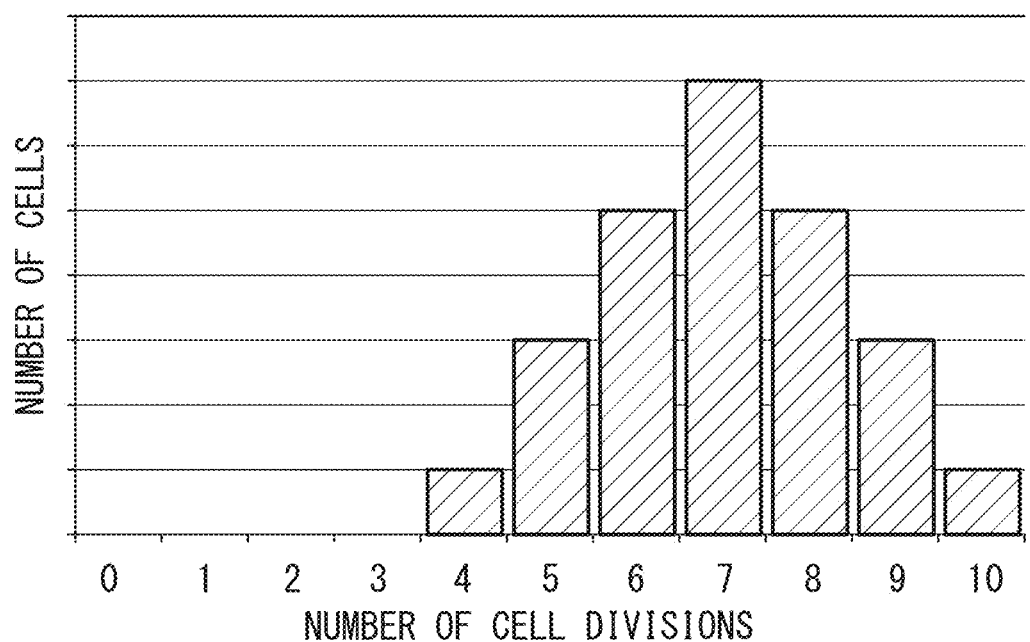
FIG. 17B illustrates an example of a cell-division frequency histogram of a cell group with high differentiation potency.

FIG. 17A illustrates a cell-division frequency histogram of a cell group with low differentiation potency (i.e., with a small number of cell divisions). FIG. 17B illustrates a cell-division frequency histogram of a cell group with high differentiation potency. The two histograms are different from each other in terms of different numbers of cell divisions, but are similar to each other in terms of their shapes. Since skewness is an indicator indicating the shape of a distribution, it is difficult to clearly discern a difference in differentiation potency between the two cell groups based on the skewness. On the other hand, since the average value of the number of cell divisions is an indicator directly indicating the number of cell divisions experienced by each cell group, it is possible to clearly discern the difference in differentiation potency between the two cell groups based on the average value.

Figure 18A:
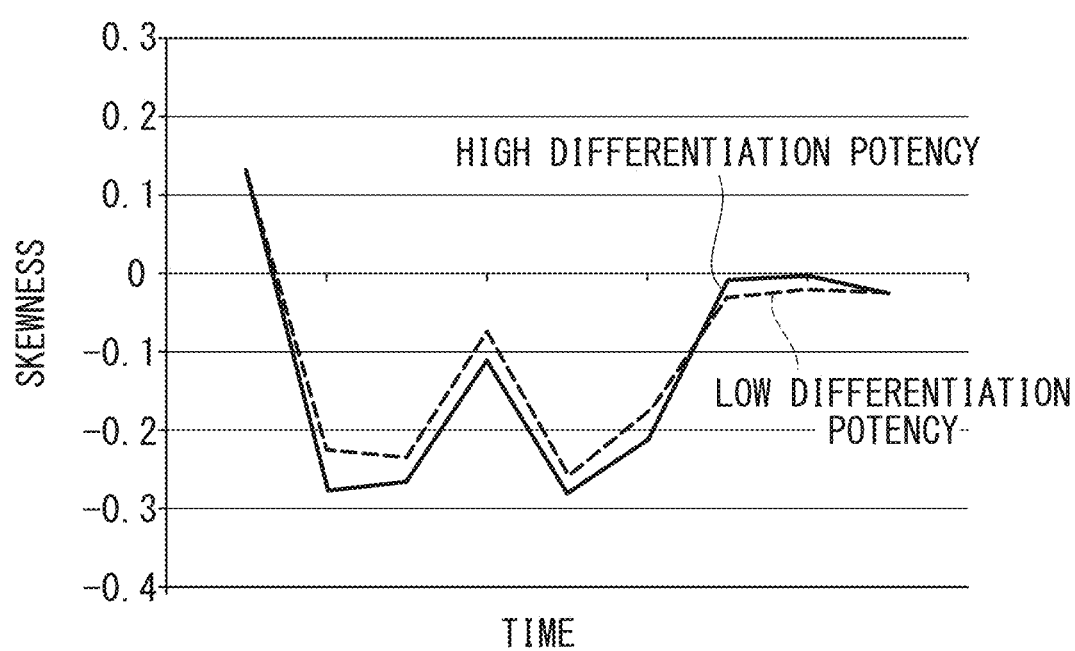
FIG. 18A illustrates an example of a graph indicating a temporal change in the skewness of a histogram for two cell groups with different differentiation potency.
Figure 18B:
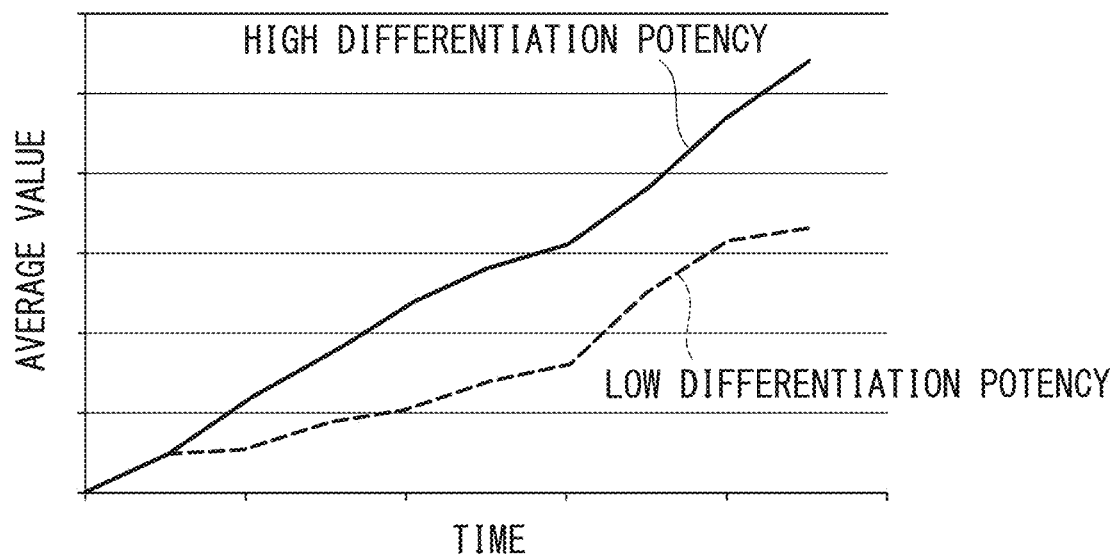
FIG. 18B illustrates an example of a graph indicating a temporal change in an average value of a histogram for two cell groups with different differentiation potency.
Figure 18C:
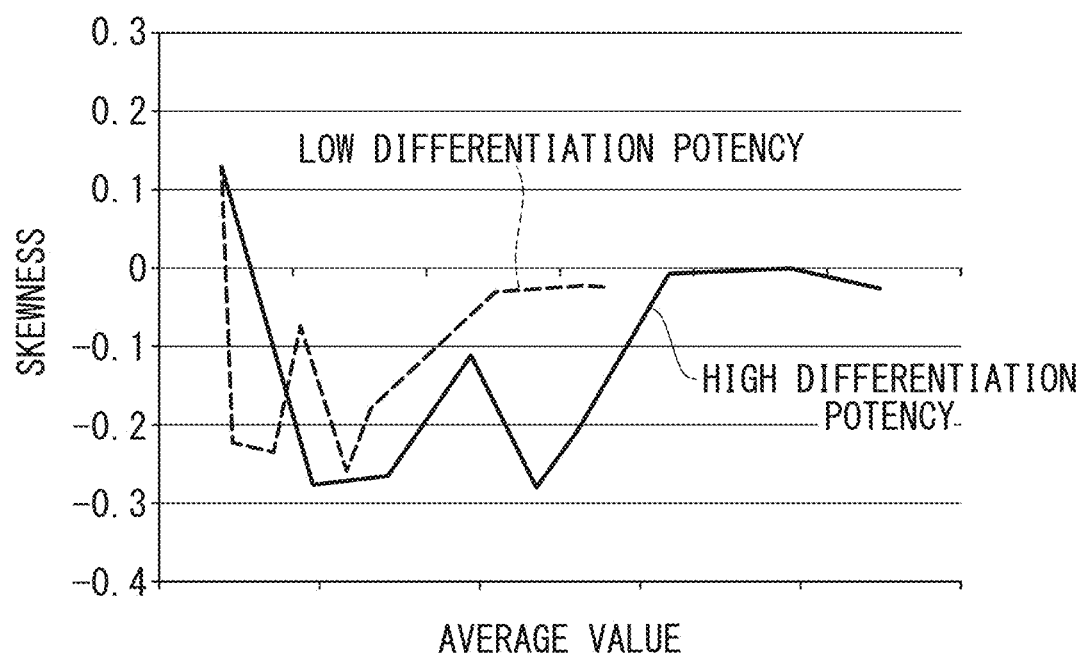
FIG. 18C is a graph indicating the relationship between the average value and the skewness.

As shown in FIG. 10, the statistical analyzer 25 creates a cell-division frequency histogram for each imaging time point and calculates the skewness and the average value of the histogram for each imaging time point. FIG. 18A is a graph indicating a temporal change in the skewness. FIG. 18B is a graph indicating a temporal change in the average value. FIG. 18C is a graph indicating a change in the skewness relative to a change in the average value. In FIGS. 18A to 18C, a solid line indicates a cell group with high differentiation potency, whereas a dashed line indicates a cell group with low differentiation potency.

As shown in FIG. 18A, the temporal changes in the skewness of the two cell groups resemble each other. On the other hand, as shown in FIG. 18B, the average value for the cell group with the high differentiation potency increases as the culturing time elapses, whereas the average value for the cell group with the low differentiation potency or not undergoing cell division increases gently as the culturing time elapses. Therefore, by combining the skewness with the average value, the levels of differentiation potency of the cells B can be evaluated more accurately.

Figure 19:
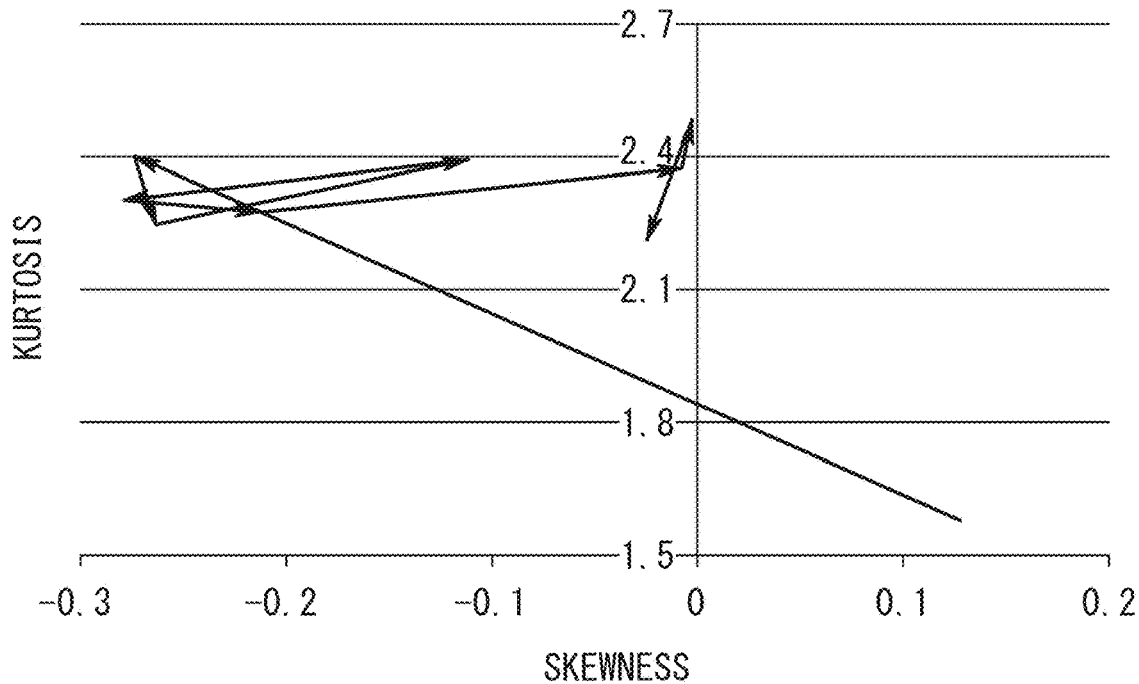
FIG. 19 is a graph indicating the relationship between skewness and kurtosis in a cell-division frequency histogram.

FIG. 19 illustrates an example of a combination of skewness and kurtosis.

A kurtosis is a statistical value indicating the sharpness of a distribution. The kurtosis Kurt is calculated in accordance with Expression (5) indicated below. Alternatively, the unbiased kurtosis Kurt defined in Expression (5') may be calculated.

{Expression 7}

$$Kurt = \frac{\sum_{k=0}^{k_{max}}(k-\mu)^4 N_k}{N\sigma^4} \quad (5)$$

{Expression 8}

$$Kurt = \frac{N(N+1)}{(N-1)(N-2)(N-3)} \frac{\sum_{k=0}^{k_{max}}(k-\mu)^4 N_k}{\sigma^4} - \frac{3(3N-5)}{(N-2)(N-3)} \quad (5')$$

Figure 20:
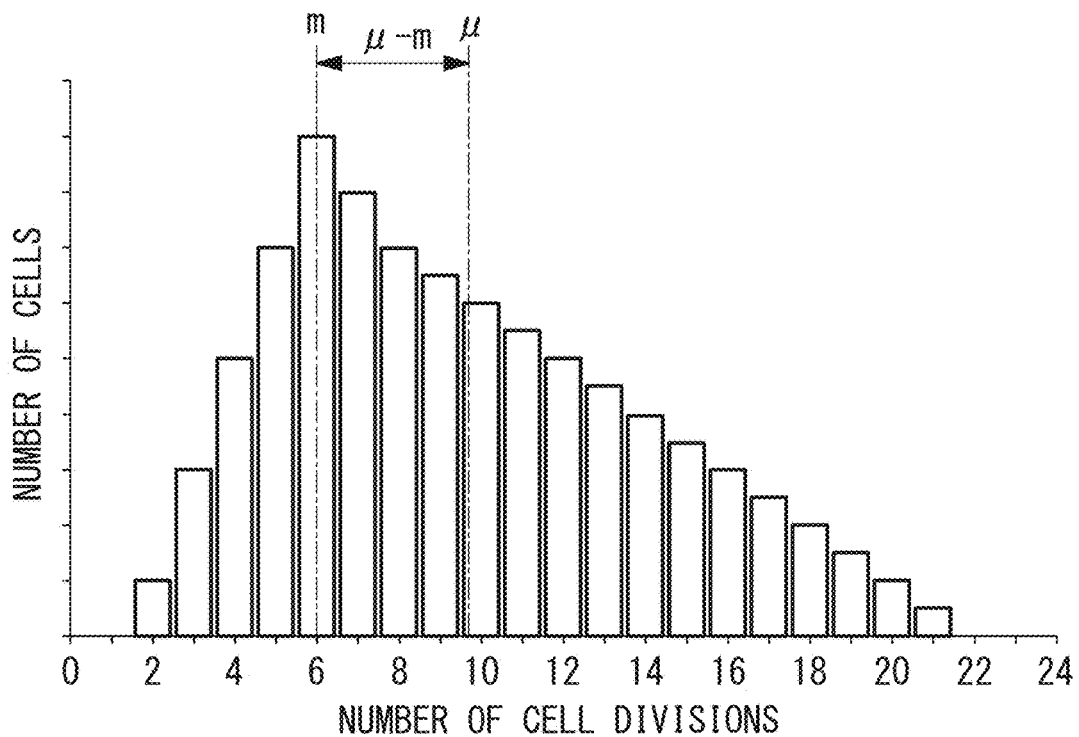
FIG. 20 illustrates another example of a cell-division frequency histogram indicating an average value and a mode value.

As an alternative to or in addition to this embodiment in which the statistical analyzer 25 calculates the skewness as a statistical value indicating a bias in a histogram, another type of statistical value may be calculated. For example, as shown in FIG. 20, another statistical value is the difference (μ–m) between an average value p and a mode value m of a histogram. When there is a bias in a distribution, a difference occurs between the average value μ and the mode value m. Therefore, based on the difference (μ–m), the differentiation potency of the cells B within the culture container A can be evaluated.

The statistical value may be two differences among any of the average value, the mode value, and the median value.

Figure 21:
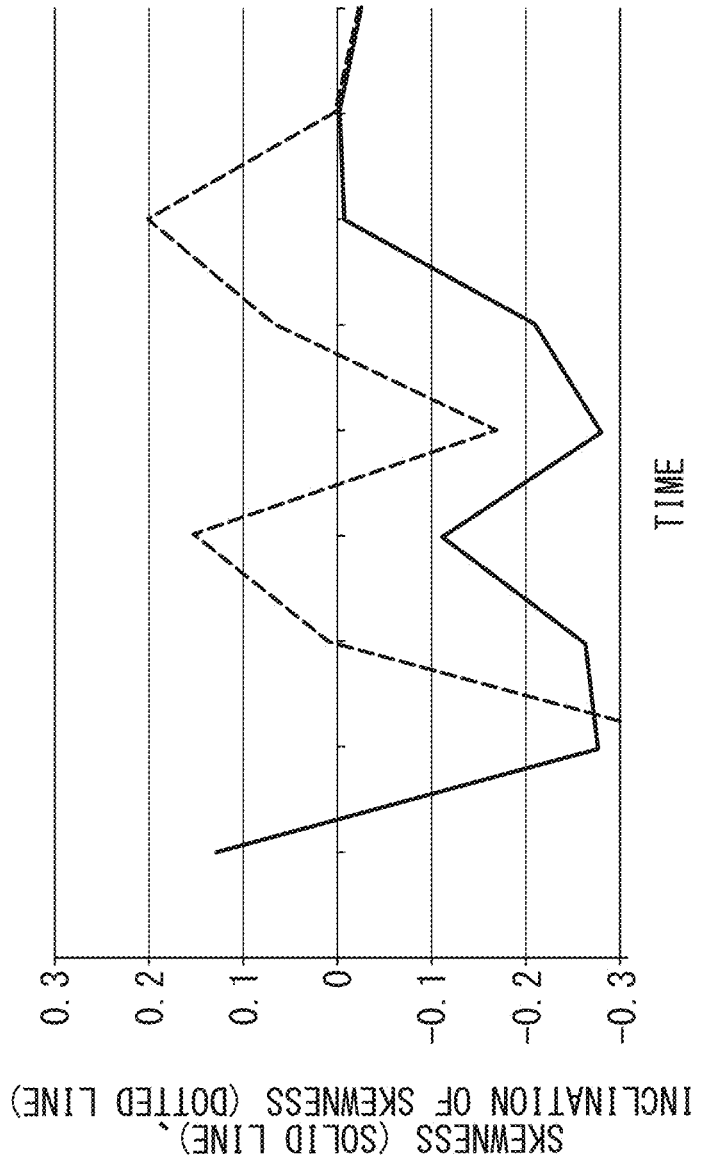
FIG. 21 illustrates an example of a graph indicating temporal changes in the skewness and the inclination of the skewness.

In this embodiment, the statistical analyzer 25 may calculate an inclination indicating a temporal change rate of the skewness, as shown in FIG. 21, in addition to the skewness. In FIG. 21, the inclination of the skewness at an imaging time point ti is defined as a difference between the skewness at an imaging time point (ti–1) and the skewness at the imaging time point ti.

The division potential of the cells B may change as the culturing time elapses. The inclination of the skewness also changes in accordance with a temporal change in the division potential of the cells B. For example, when the number of cells B that do not divide increases as the culturing time elapses, the inclination of the skewness becomes positive. Therefore, based on the inclination of the skewness, a temporal change in the division potential of the cells B can be evaluated.

Second Embodiment

Next, a culture evaluation system according to a second embodiment of the present invention will be described with reference to the drawings.

In the description of this embodiment, components different from those in the first embodiment will be described, whereas components identical to those in the first embodiment will be given the same reference signs and will not be described.

In the first embodiment, the operator evaluates the status of the cells B based on the operator's own experience up to that point. In contrast, a culture evaluation system 200 according to this embodiment differs from that in the first embodiment in that it retains reference data to be compared with a statistical value and displays the reference data together with the statistical value on the display 3.

Figure 22:
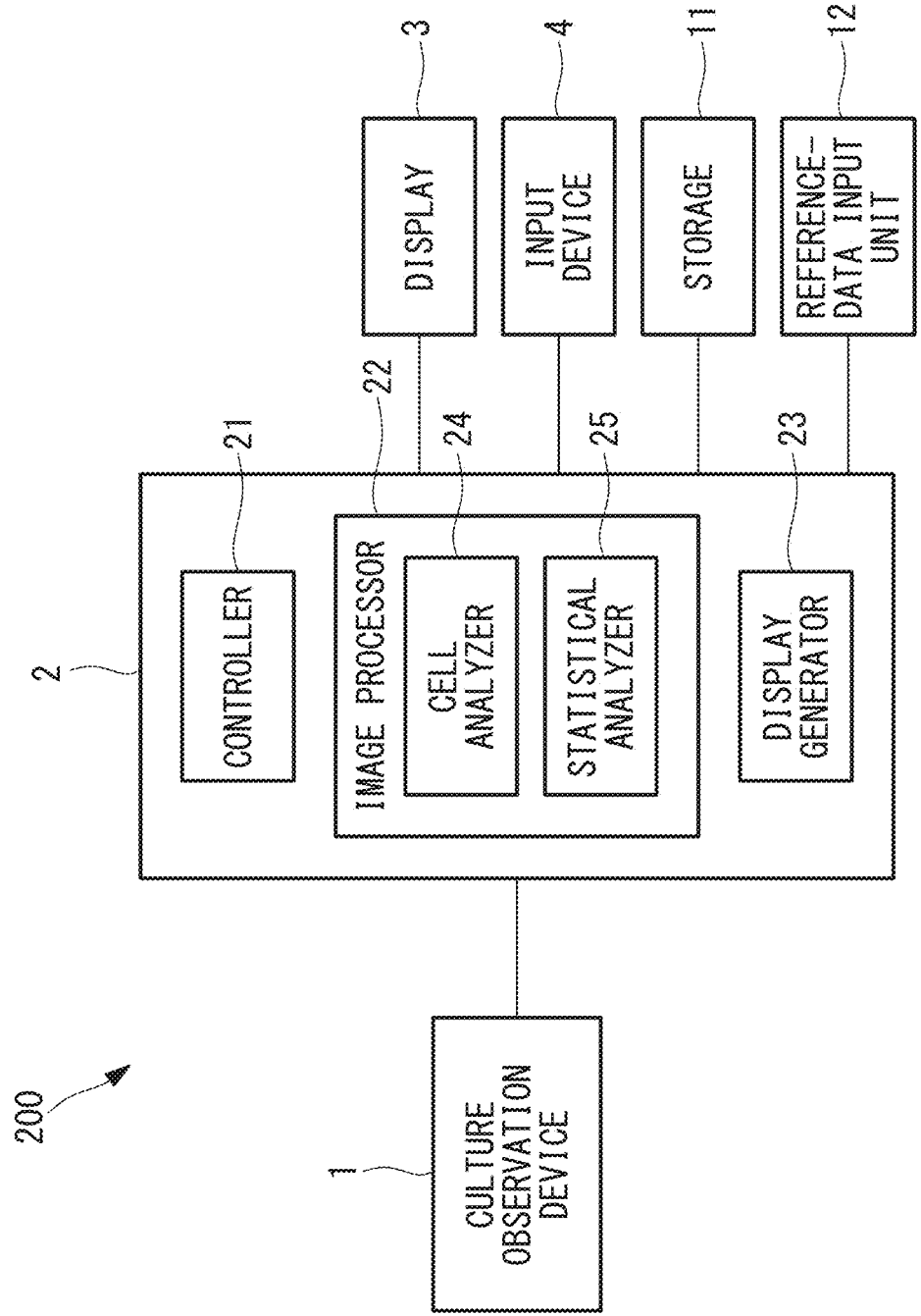
FIG. 22 is a block diagram illustrating the overall configuration of a culture evaluation system according to a second embodiment of the present invention.

As shown in FIG. 22, the culture evaluation system 200 includes the culture observation device 1, the PC 2, the display 3, the storage 11, and a reference-data input unit 12.

The reference-data input unit 12 is, for example, the input device 4 connected to the PC 2. The operator can input the reference data to the PC 2 by using the reference-data input unit 12. The reference data input to the PC 2 is stored in the storage 11. The reference data includes, for example, a standard statistical value set based on the operator's experience up to that point. The reference data may contain a maximum value and a minimum value within a standard range of the statistical value or may contain a graph indicating a temporal change in the statistical value.

The display generator 23 generates display data used for comparing the statistical value calculated by the statistical analyzer 25 with the reference data. The display generator 23 transmits the generated display data to the display 3 where the display data is displayed.

This embodiment exhibits the following advantages in addition to the advantages of the first embodiment. Specifically, the operator compares the statistical value and the reference data displayed on the display 3 so as to objectively evaluate the status of the cells B. Therefore, even a less experienced operator can accurately evaluate the status of the cells B, and variations in the evaluation of the status of the cells B caused by different operators can be prevented, so that an experiment with high reproducibility can be performed.

Third Embodiment

Next, a culture evaluation system according to a third embodiment of the present invention will be described with reference to the drawings.

In the description of this embodiment, components different from those in the first and second embodiments will be described, whereas components identical to those in the first and second embodiments will be given the same reference signs and will not be described.

In the second embodiment, the operator evaluates the status of the cells B based on a comparison result of the statistical value and the reference data displayed on the display 3. In contrast, a culture evaluation system 300 according to this embodiment differs from that in the second embodiment in that it determines the differentiation potency of the cells B based on the comparison result of the statistical value and the reference data and displays the determination result on the display 3.

Figure 23:
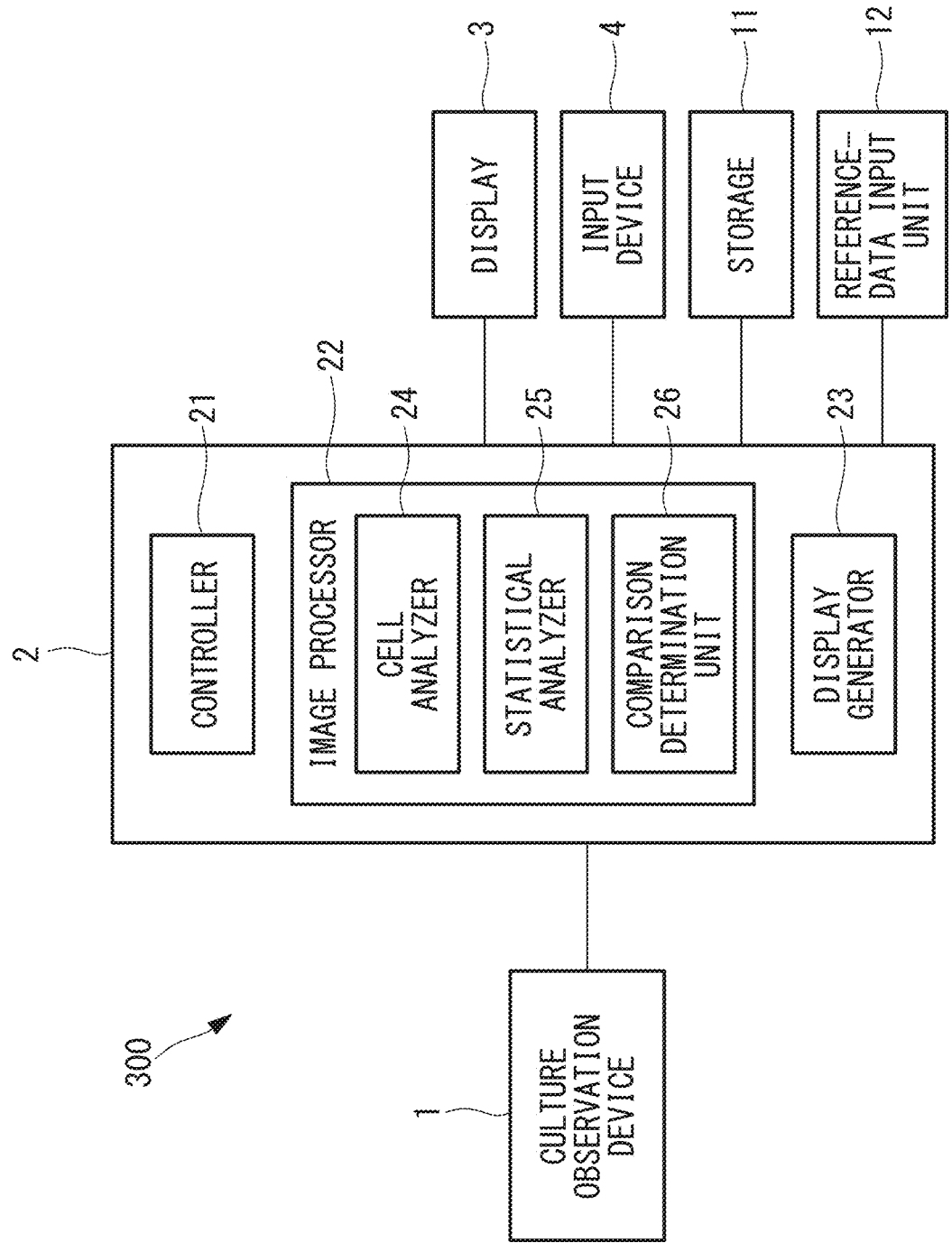
FIG. 23 is a block diagram illustrating the overall configuration of a culture evaluation system according to a third embodiment of the present invention.

As shown in FIG. 23, the culture evaluation system 300 includes the culture observation device 1, the PC 2, the display 3, the storage 11, and the reference-data input unit 12.

The image processor 22 in the PC 2 includes a comparison determination unit 26 in addition to the cell analyzer 24 and the statistical analyzer 25.

The comparison determination unit 26 reads the reference data from the storage 11 and compares the statistical value calculated by the statistical analyzer 25 with the reference data.

Figure 24A:
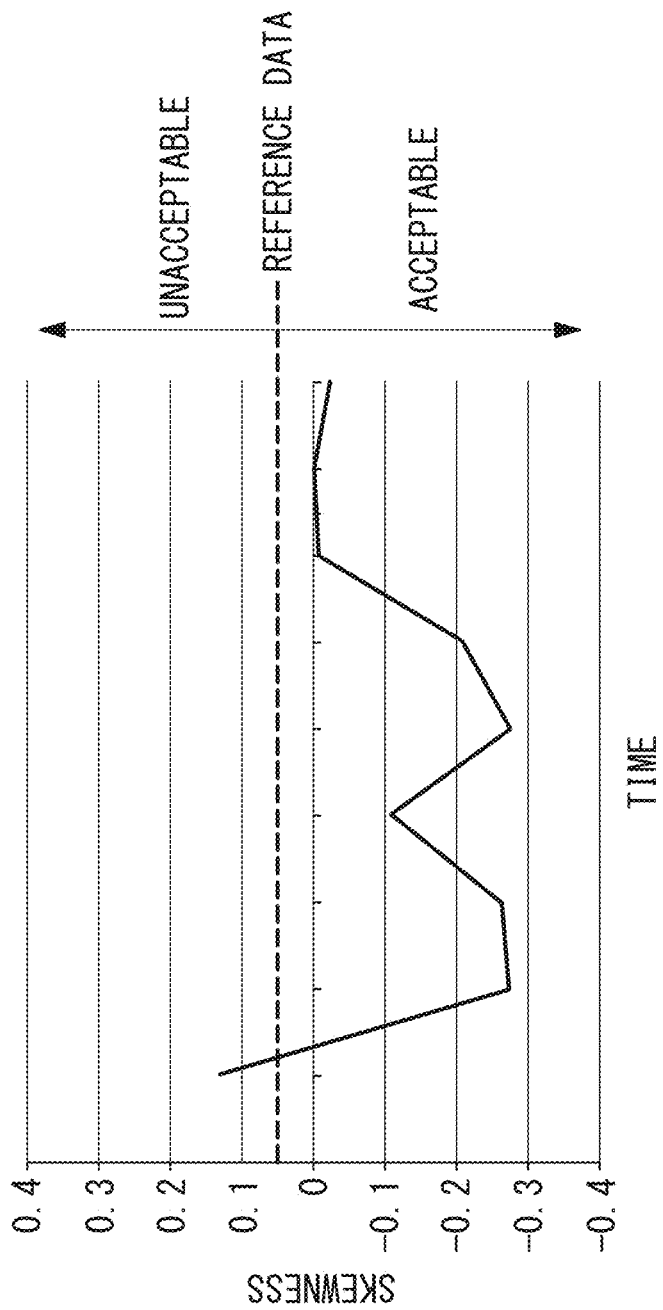
FIG. 24A illustrates an example of reference data and a method of how a comparison determination unit determines whether a culturing process is acceptable or unacceptable.

For example, as shown in FIG. 24A, the reference data is a standard statistical value. The comparison determination unit 26 determines that the statistical value is acceptable if it is smaller than or equal to the reference data, and determines that the statistical value is unacceptable if it is larger than the reference data.

Figure 24B:
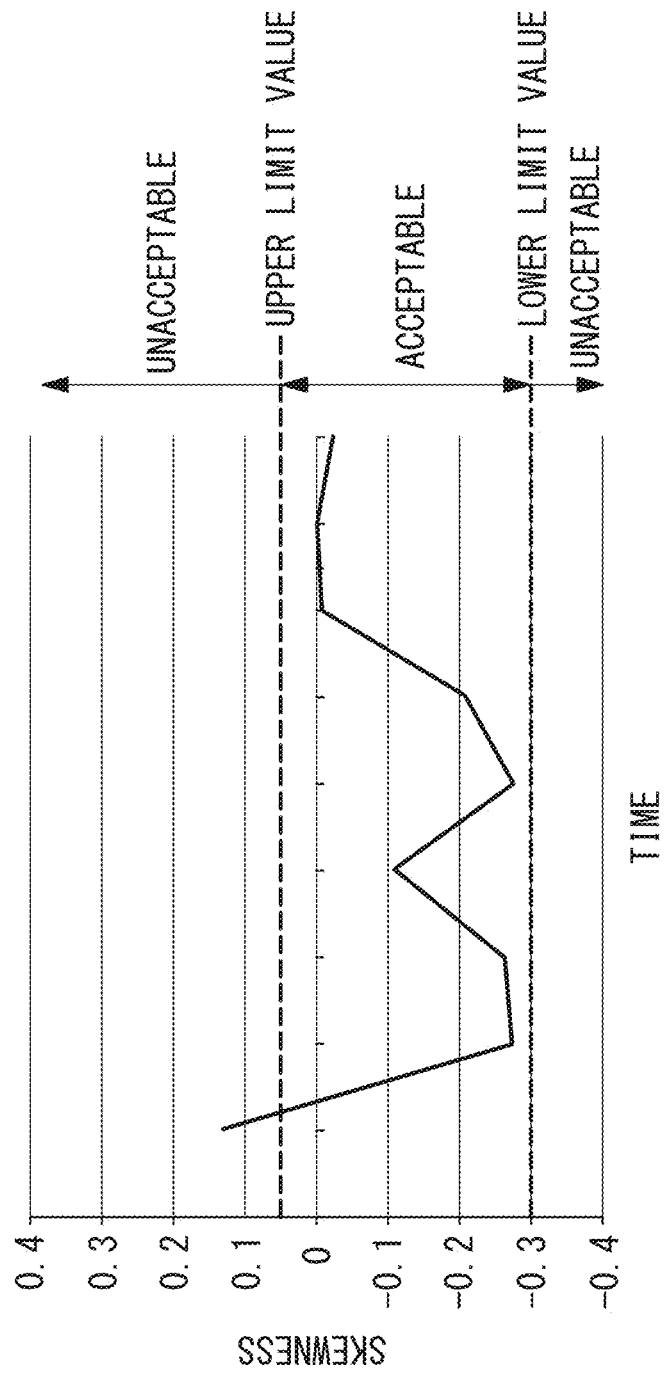
FIG. 24B illustrates another example of the reference data and the method of how the comparison determination unit determines whether a culturing process is acceptable or unacceptable.
Figure 24C:
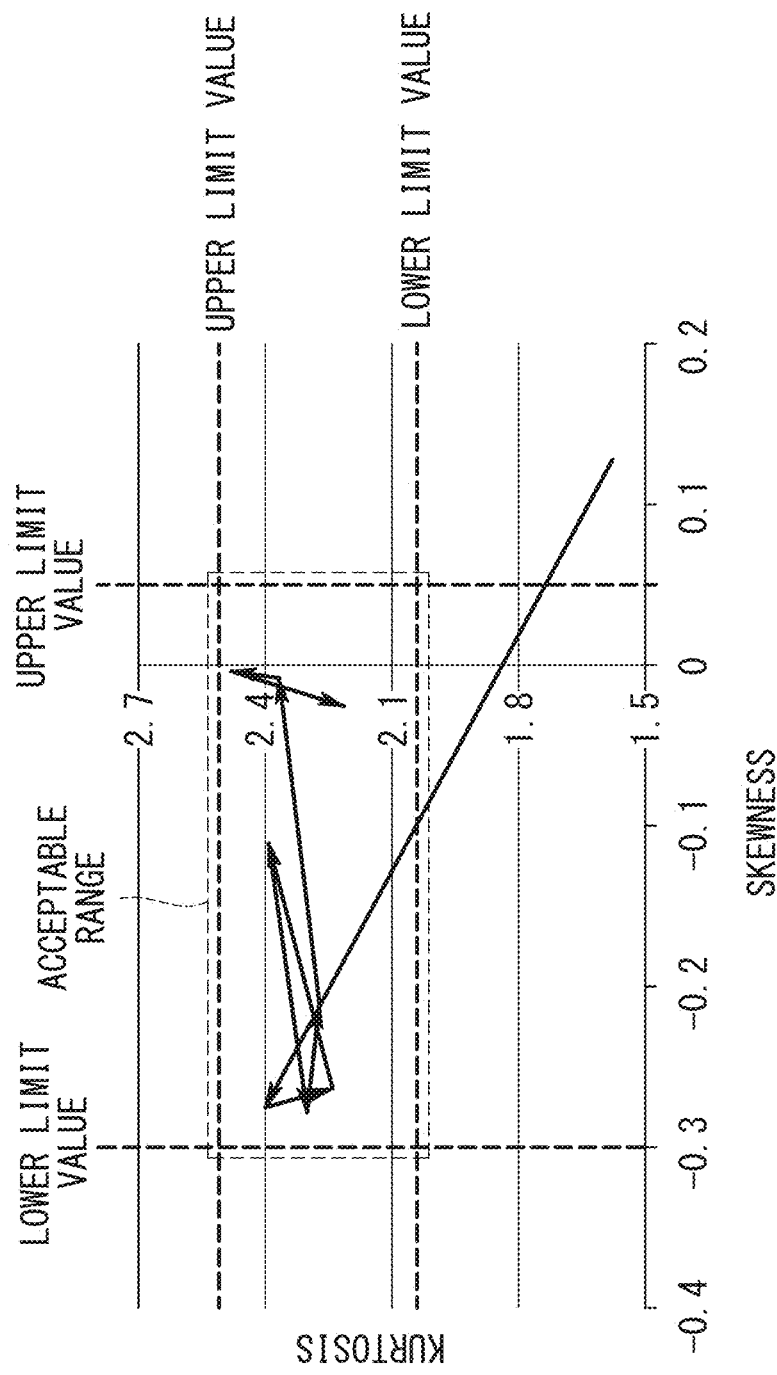
FIG. 24C illustrates another example of the reference data and the method of how the comparison determination unit determines whether a culturing process is acceptable or unacceptable.

As shown in FIGS. 24B and 24C, the reference data may include an upper limit value and a lower limit value for the statistical value. The upper limit value and the lower limit value define an acceptable culture range. In this case, the comparison determination unit 26 may determine that the statistical value is acceptable if it is within the acceptable range, and may determine that the statistical value is unacceptable if it is outside the acceptable range. The upper limit value and the lower limit value are set by the operator. For example, the upper limit value and the lower limit value are set based on the operator's experience or based on a measurement result of the differentiation potency of cells cultured in the past.

The display generator 23 generates display including the statistical value and the determination result obtained by the comparison determination unit 26, transmits the generated display to the display 3 where the generated display is displayed.

This embodiment exhibits the following advantages in addition to the advantages of the first and second embodiments. Specifically, the culture evaluation system 300 determines whether the current culturing process is acceptable or unacceptable based on the comparison between the statistical value in the current culturing process and the reference data. Based on the statistical value and the determination result displayed on the display 3, the operator can evaluate the status of the cells B more objectively.

Fourth Embodiment

Next, a culture evaluation system according to a fourth embodiment of the present invention will be described with reference to the drawings.

In the description of this embodiment, components different from those in the first to third embodiments will be described, whereas components identical to those in the first to third embodiments will be given the same reference signs and will not be described.

In the third embodiment, the reference data is input by the operator. In contrast, a culture evaluation system 400 according to this embodiment differs from that in the third embodiment in that it creates the reference data based on an evaluation result of cultured cells B.

Figure 25:
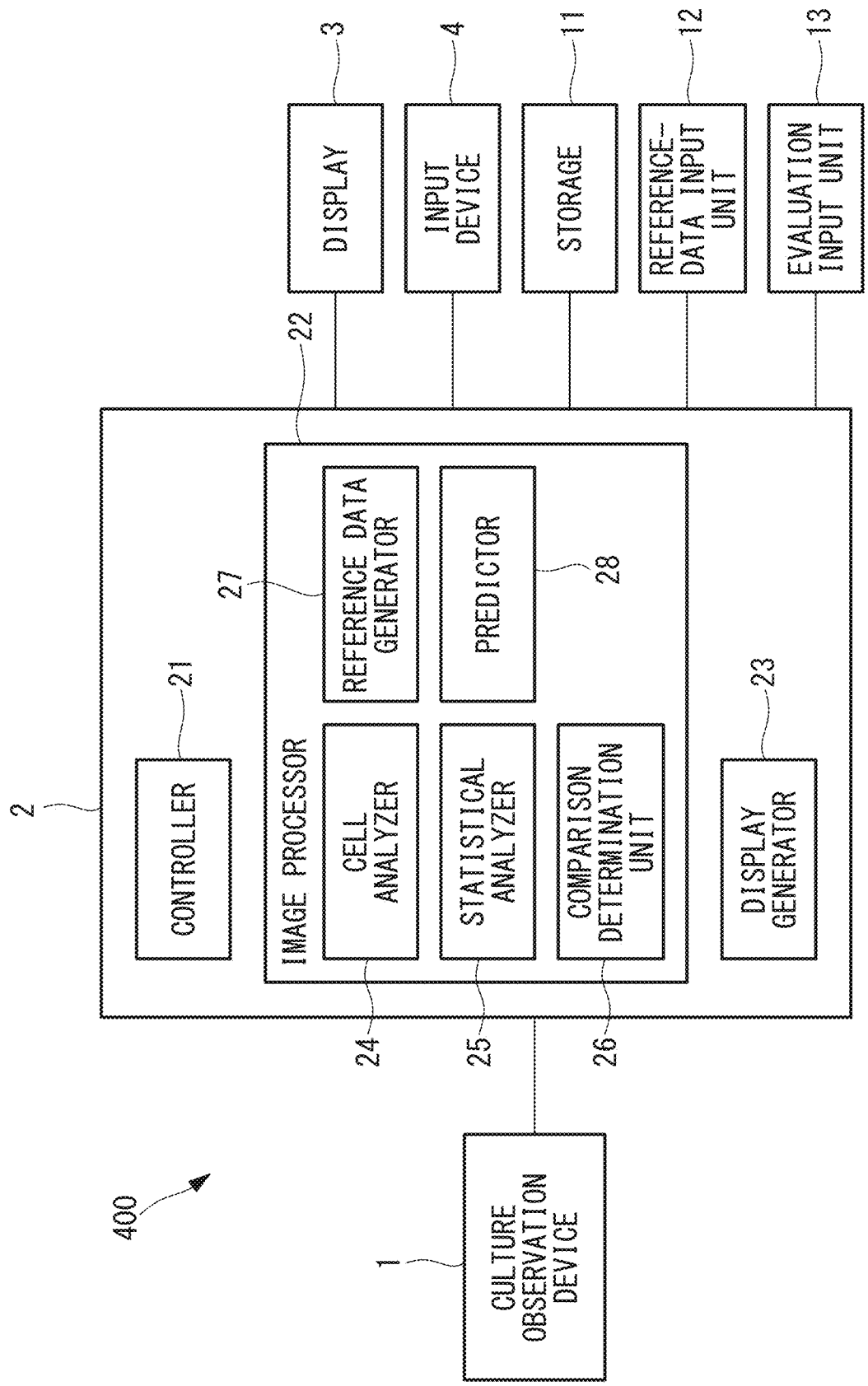
FIG. 25 is a block diagram illustrating the overall configuration of a culture evaluation system according to a fourth embodiment of the present invention.

As shown in FIG. 25, the culture evaluation system 400 includes the culture observation device 1, the PC 2, the display 3, the storage 11, the reference-data input unit 12, and an evaluation input device 13.

The evaluation input device 13 is, for example, the input device 4. The operator can use the evaluation input device 13 to input an evaluation result of cultured cells B in association with a culture identifier. The operator evaluates whether the differentiation potency of the cells B is good or poor based on whether an experiment using the cultured cells B is successful or unsuccessful, and inputs the evaluation result to the evaluation input device 13. The input evaluation result is transmitted from the PC 2 to the storage 11 and is stored in the database in the storage 11 in association with a culture identifier, as shown in FIG. 26.

In addition to the identifier, the imaging start time, the imaging position of each image, the imaging time point, and the analysis result, current and future determination results (to be described later) and an evaluation result obtained after an experiment are stored in association with each other in the database in the storage 11.

In addition to the cell analyzer 24, the statistical analyzer 25, and the comparison determination unit, the image processor 22 in the PC 2 further includes a reference data generator 27 and a predictor 28.

The reference data generator 27 reads statistical-value data, which have been acquired in past culturing processes, stored in the storage 11 and generates reference data from statistical-value data of a culturing process corresponding to a successful experiment (i.e., a good evaluation result of cultured cells B), and generates reference data from statistical-value data of a culturing process corresponding to an unsuccessful experiment (i.e., a poor evaluation result of cultured cells B). An example of reference data is a list of statistical values. Reference data may be generated by means of, for example, polynomial approximation, support vector machine (SVM), deep learning, or averaging of a plurality of statistical values.

Figure 27:
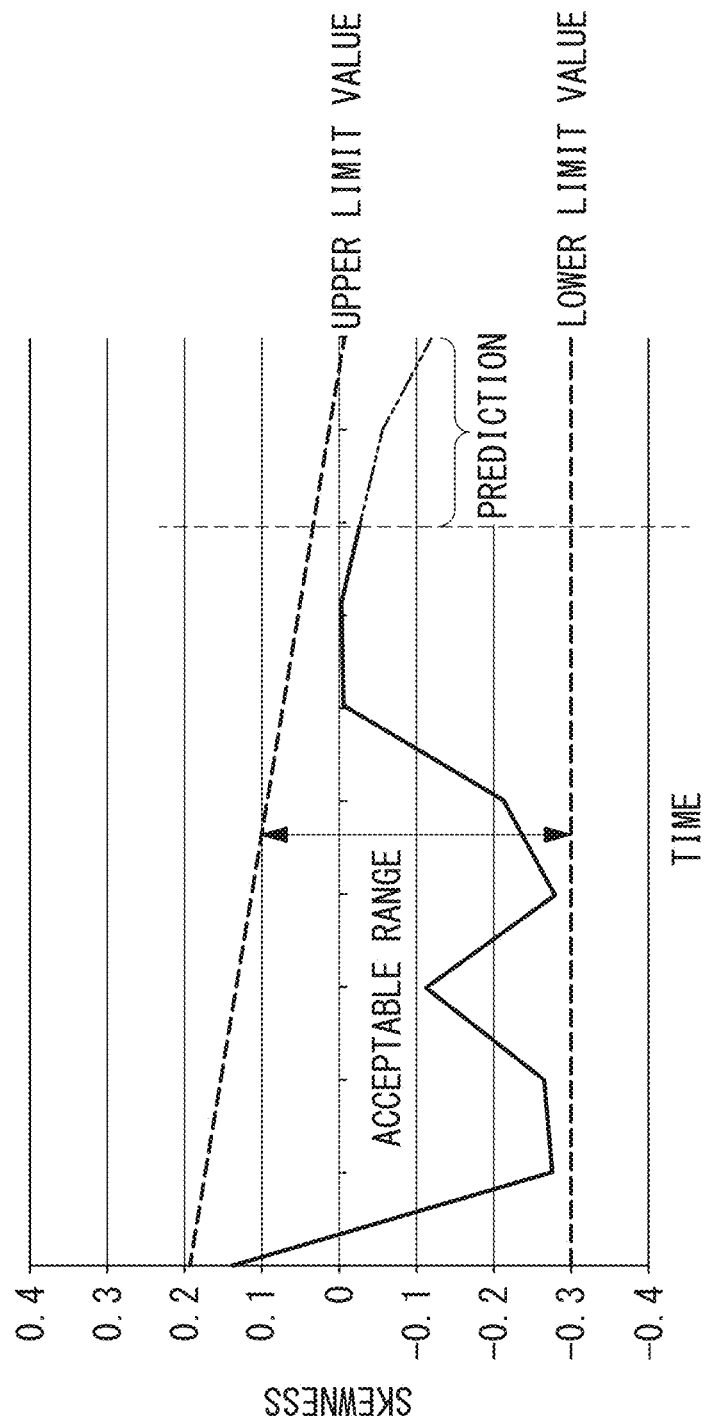
FIG. 27 illustrates an example of display generated by a display generator of the culture evaluation system in FIG. 25.

For example, as shown in FIG. 27, the reference data generator 27 determines the boundary between a statistical value of a culturing process corresponding to a successful experiment and a statistical value of a culturing process corresponding to an unsuccessful experiment, that is, an upper limit value and a lower limit value for the statistical value of the culturing process corresponding to the successful experiment, sets the range between the lower limit value and the upper limit value as an acceptable culture range, and sets the range outside the acceptable range as an unacceptable range.

For example, when a new cell evaluation result is stored in the storage 11 or when a command is given by the operator, the reference data generator 27 generates reference data, sets an acceptable range and an unacceptable range, and stores the reference data, the acceptable range, and the unacceptable range in the storage 11.

When a new image is acquired by the culture observation device 1 and a current statistical value is calculated by the statistical analyzer 25, the predictor 28 reads current culturing statistical values up to that point from the storage 11 and predicts a future statistical value from the read statistical values. For example, the predictor 28 predicts a statistical value after a predetermined time period from the current time point or at a subsequent imaging time point by the culture observation device 1. For predicting a statistical value, for example, polynomial-approximation-based extrapolation of a graph indicating temporal changes in statistical values up to that point may be used, or deep learning using a recurrent neural network based on temporal changes in statistical values from past culturing processes may be used.

When a new image is acquired by the culture observation device 1 and a current statistical value is calculated by the statistical analyzer 25, the comparison determination unit 26 compares the current statistical value with the acceptable range, and determines that the current statistical value is acceptable if it is within the acceptable range or determines that the current statistical value is unacceptable if it is outside the acceptable range.

Furthermore, the comparison determination unit 26 receives the future statistical value from the predictor 28, compares the future statistical value with the acceptable range, and determines that the future statistical value is acceptable if it is within the acceptable range or determines that the future statistical value is unacceptable if it is outside the acceptable range.

The current and future determination results obtained by the comparison determination unit 26 are stored in the database in the storage 11.

As shown in FIG. 27, the display generator 23 generates display data in which a graph indicating a temporal change in the statistical value in the current culturing process is combined with the reference data. The display generator 23 may add the future statistical value predicted by the predictor 28 to the statistical-value graph.

This embodiment exhibits the following advantages in addition to the advantages of the first to third embodiments. Specifically, statistical values from past culturing processes are stored in the storage 11 in association with culture evaluation results based on whether experiments using cultured cells B are successful or unsuccessful, so that a statistical value of a culturing process corresponding to a successful experiment and a statistical value of a culturing process corresponding to an unsuccessful experiment are accumulated. Then, based on the accumulated statistical values, reference data serving as a model of temporal changes in the statistical values of the culturing processes corresponding to the successful and unsuccessful experiments is generated. The comparison determination unit 26 compares the current and future statistical values with the reference data, so that the current and future statuses of the cells B can be evaluated more accurately.

Consequently, the operator can objectively evaluate the status of the cells B based on the current statistical value displayed on the display 3 and the determination result obtained by the comparison determination unit 26. Specifically, even a less experienced operator can accurately evaluate the status of the cells B, and variations in the evaluation of the status of the cells B caused by different operators can be prevented, so that an experiment with high reproducibility can be performed.

As an alternative to the above-described embodiments in which the cell analyzer 24 tracks the cells B in the image to acquire the number of cell divisions experienced by each cell B, the number of cell divisions may be acquired based on the fluorescence intensity of each cell B in the image.

Figure 28:
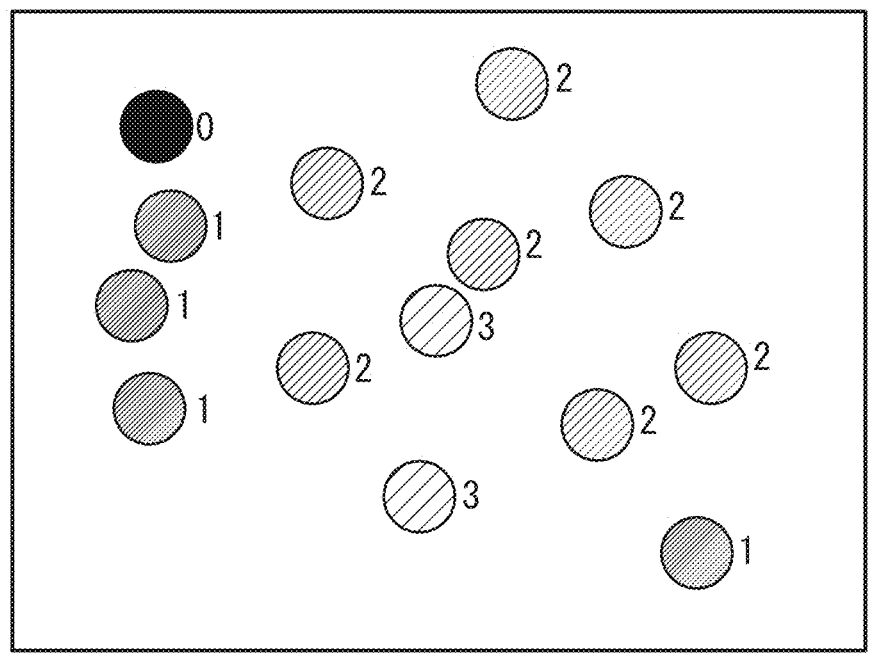
FIG. 28 illustrates another example of a method of how the cell analyzer analyzes the number of cell divisions.

For example, the number of cell divisions experienced by each cell B may be measured by using carboxyfluorescein succinimidyl ester (CFSE) dilution. CFSE is a fluorescent dye. The fluorescence intensity of a cell which has incorporated CFSE decreases by half every time the cell undergoes cell division, as shown in FIG. 28. Therefore, the number of cell divisions experienced by each cell B can be estimated from the fluorescence intensity of the CFSE in the cell B. In FIG. 28, each circle indicates a single cell B, the differences in hatch patterns indicate differences in the fluorescence intensity, and each numerical value indicates the number of cell divisions.

Figure 29:
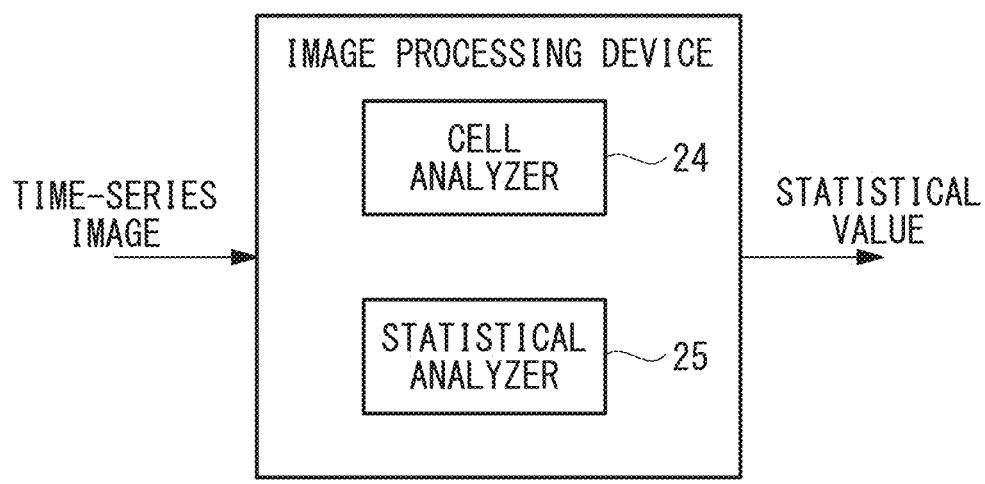
FIG. 29 is a block diagram illustrating the overall configuration of an image processing device according to another embodiment of the present invention.

As an alternative to the above-described embodiments in which the image processing device is realized as a part of the PC 2 in the culture evaluation system 100, 200, 300, or 400, the image processing device may be realized as an independent device, as shown in FIG. 29. For example, the image processing device may receive a time-series image acquired in the past by the culture observation device 1, calculate a statistical value by analyzing the time-series image, and output the statistical value to an external device.

As an alternative to the above-described embodiments in which the differentiation potency of cultured cells is evaluated based on a statistical value for the purpose of selecting cells having predetermined differentiation potency, the statistical value serving as an indicator for the differentiation potency of cells can be used for other purposes.

For example, an effect of an external factor that affects the differentiation potency of cells, such as a culture medium component or a differentiation/non-differentiation-inducing reagent, can be quantitatively examined based on the statistical value.

For example, a cell group cultured within a single culture container and expected to have the same differentiation potency is separated into two condition groups. One of the condition groups is cultured under a normal culturing condition, whereas the other condition group is cultured in a reagent-added culture medium. The statistical values of the two condition groups are calculated. Then, based on a difference between the statistical values of the two condition groups, the effect of the added reagent can be quantitatively examined.

Furthermore, each of the condition groups is cultured using a multi-well plate, and the cells in the wells are determined as being acceptable or unacceptable by using the method according to the present invention. Then, the effect of the added reagent can be quantified in accordance with the percentage of the number of wells determined as being acceptable.

From the above-described embodiments, the following aspects of the present disclosure are derived.

An aspect of the present invention provides an image processing device including a cell analyzer and a statistical analyzer. The cell analyzer analyzes an image of cells cultured within a culture container and acquires the number of cell divisions experienced by each cell in the image. The statistical analyzer calculates a statistical value indicating differentiation potency of each cell in the image from the number of cell divisions acquired by the cell analyzer. The statistical analyzer creates a frequency distribution of the number of cell divisions, and the statistical value represents a bias in the frequency distribution.

According to this aspect, the cell analyzer analyzes the image within the culture container so as to acquire the number of cell divisions experienced by each cell within the culture container. Then, the statistical analyzer statistically analyzes the number of cell divisions so as to calculate the statistical value indicating a bias in the cell-division frequency distribution.

If the cells are repeatedly undergoing satisfactory cell divisions within the culture container, the frequency distribution would not be biased (i.e., have a symmetrical shape) or may be biased toward the side with the larger number of cell divisions. On the other hand, if the cells are dead or have stopped dividing within the culture container, the frequency distribution may be biased toward the side with the smaller number of cell divisions.

Therefore, it can be determined whether or not the cells are repeatedly undergoing satisfactory cell divisions within the culture container based on the statistical value indicating a bias in the cell-division frequency distribution, and the status, specifically, the differentiation potency, of the cells cultured within the culture container can be readily evaluated. In addition, the differentiation potency of the cells can be evaluated concurrently with the expansion culturing process by using the normal image of the cells being expansion-cultured. Moreover, every time an experiment is to be performed, the operator can evaluate the status of the cells within the culture container based on the statistical value and can perform the experiment by selectively using cells suitable for the experiment. This can contribute to improved reproducibility of the experiment.

Another aspect of the present invention provides a culture evaluation system including an image sensor and an image processing device. The image sensor acquires an image of cells cultured within a culture container. The image processing device processes the image acquired by the image sensor. The image processing device includes a cell analyzer and a statistical analyzer. The cell analyzer analyzes the image and acquires the number of cell divisions experienced by each cell in the image. The statistical analyzer calculates a statistical value indicating differentiation potency of each cell in the image from the number of cell divisions acquired by the cell analyzer. The statistical analyzer creates a frequency distribution of the number of cell divisions, and the statistical value represents a bias in the frequency distribution.

In the above aspect, the statistical analyzer may calculate a skewness in the frequency distribution as the statistical value.

By using the skewness as the statistical value, a bias in the cell-division frequency distribution can be evaluated more accurately.

In the above aspect, the statistical analyzer may further calculate at least one of an average value, a median value, a mode value, a variance, and a kurtosis of the frequency distribution as the statistical value.

By combining the skewness with another statistical value, the number of cell divisions experienced by each cell within the culture container can be evaluated more accurately.

In the above aspect, the cell analyzer may create a frequency distribution indicating the number of cells corresponding to each number of cell divisions as the frequency distribution.

According to this configuration, a bias in the number of cells between different numbers of cell divisions can be evaluated based on the frequency distribution in which the number of cells is defined as a frequency.

In the above aspect, the number of cells corresponding to each number of cell divisions may be a converted numerical value converted into a state of staring a culturing process.

The number of cell divisions experienced by each cell increases with increasing culturing period. Therefore, if the frequency of the number of cell divisions in the frequency distribution is the number of cells corresponding to each number of cell divisions in the image, the statistical value varies in accordance with the length of the culturing period. Therefore, it is difficult to simply compare statistical values between a plurality of cultures with different lengths of culturing periods. By converting the frequency into the number of cells at the start of the culturing process, the statistical values can be readily compared between a plurality of cultures with different lengths of culturing periods.

In the above aspect, the cell analyzer may divide the image into a plurality of regions and acquire the number of cell divisions experienced by each cell within each region. The statistical analyzer may calculate a representative value of the number of cell divisions in each region, and create a frequency distribution indicating the number of regions with the corresponding representative values as the frequency distribution.

If cells have experienced a significantly large or small number of cell divisions, as compared with surrounding cells, exist locally within the culture container, the representative value of the number of cell divisions in one region significantly varies from the representative value in another region. Such a spatial variation in the number of cell divisions within the culture container can be evaluated based on the statistical value of the frequency distribution in which the number of regions with the representative values is defined as a frequency.

In the above aspect, the culture evaluation system may further include a storage that stores reference data of the statistical value, and a display that displays the statistical value and the reference data in a comparable manner.

By comparing the statistical value and the reference data displayed on the display, the status of the cells can be evaluated objectively.

In the above aspect, the image sensor may sequentially acquire images within the culture container. The statistical analyzer may calculate a temporal change in the statistical value. The display may display the temporal change in the statistical value and the reference data in a comparable manner.

With this configuration, the operator can evaluate temporal changes in the division potential and the differentiation potency of the cells within the culture container based on a temporal change in the statistical value. Furthermore, the operator can readily compare the temporal change in the statistical value with the reference data.

In the above aspect, the culture evaluation system may further include a comparison determination unit that determines the differentiation potency of each cell within the culture container based on a comparison between the statistical value calculated by the statistical analyzer and the reference data.

With this configuration, the operator can evaluate the differentiation potency of the cells more objectively based on the determination result of the differentiation potency obtained by the comparison determination unit.

In the above aspect, the storage may further store therein the statistical value calculated by the statistical analyzer.

With this configuration, the statistical value stored in the storage can be used in, for example, an analysis.

In the above aspect, the reference data may include a lower limit value and an upper limit value set for the statistical value. The comparison determination unit may determine the differentiation potency of each cell within the culture container based on a comparison between the statistical value calculated by the statistical analyzer and the upper limit value and the lower limit value.

With this configuration, the comparison determination unit can determine the differentiation potency of the cells more appropriately.

In the above aspect, the display may display an acceptable range defined by the lower limit value and the upper limit value.

With this configuration, the operator can evaluate the differentiation potency of the cells more objectively based on a comparison between the statistical value and the acceptable range.

In the above aspect, the culture evaluation system may further include an evaluation input unit to which an evaluation result of cultured cells is input by an operator. The storage may store therein the evaluation result input to the evaluation input unit in association with the statistical value calculated by the statistical analyzer in a culturing process of the evaluated cells.

After an experiment is performed using the cultured cells, the final evaluation of the differentiation potency of the cells can be ascertained based on the experimental result. By storing this evaluation result in association with the statistical value, information related to the correlation between the evaluation result of the differentiation potency of the cells and the statistical value is accumulated in the storage. By referring to this accumulated information, the operator can more accurately evaluate the differentiation potency of the cells currently being cultured.

In the above aspect, the comparison determination unit may determine the differentiation potency of each cell within the culture container based on a comparison between a current statistical value of each cell within the culture container and the statistical value stored in the storage in association with the evaluation result and acquired in a past culturing process.

By referring to the statistical value acquired in the past culturing process and the evaluation result in this manner, the comparison determination unit can more accurately determine the differentiation potency of the cells currently being cultured.

In the above aspect, the culture evaluation system may further include a predictor that predicts a future statistical value based on a current statistical value obtained from the image of the cells within the culture container. The comparison determination unit may determine the differentiation potency of each cell in the future based on a comparison between the future statistical value predicted by the predictor and the lower limit value and the upper limit value.

According to this configuration, the operator can determine whether or not to continue with the culturing process based on the prediction result of the differentiation potency of the cells in the future.

According to the aforementioned aspects, the present invention is advantageous in that it allows for a simple evaluation of the differentiation potency of cells being cultured and that it can contribute to improved reproducibility of an experiment.

REFERENCE SIGNS LIST 1 culture observation device (image sensor)
2 personal computer
3 display
4 input device
11 storage
12 reference-data input unit
13 evaluation input device
21 controller
22 image processor (image processing device)
23 display generator
24 cell analyzer
25 statistical analyzer
26 comparison determination unit
27 reference data generator
28 predictor
100, 200, 300, 400 culture evaluation system
A culture container
B cell

The invention claimed is:

1. An image processing device comprising a processor configured to:
  analyze an image of cells cultured within a culture container and acquire the number of cell divisions experienced by each cell in the image;
  calculate a statistical value indicating differentiation potency of each cell in the image based on the number of cell divisions acquired by analyzing the image, the differentiation potency being an ability of each cell in the image to be changed into different types of cells and the number of cell divisions being how many times each cell in the image has experienced division, and
  create a frequency distribution of the number of cell divisions, and the statistical value represents a bias in the frequency distribution.

2. A culture evaluation system comprising:
an image sensor that acquires an image of cells cultured within a culture container; and
a processor configured to:
  process the image acquired by the image sensor,
  analyze the image and acquire the number of cell divisions experienced by each cell in the image;
  calculate a statistical value indicating differentiation potency of each cell in the image based on the number of cell divisions acquired by analyzing the image, the differentiation potency being an ability of each cell in the image to be changed into different types of cells and the number of cell divisions being how many times each cell in the image has experienced division, and
  create a frequency distribution of the number of cell divisions, and the statistical value represents a bias in the frequency distribution.

3. The culture evaluation system according to claim 2, wherein the processor is configured to calculate a skewness in the frequency distribution as the statistical value.

4. The culture evaluation system according to claim 3, wherein the processor is further configured to calculate at least one of an average value, a median value, a mode value, variance, and a kurtosis of the frequency distribution as the statistical value.

5. The culture evaluation system according to claim 2, wherein the processor is configured to create a frequency distribution indicating the number of cells corresponding to each number of cell divisions as the frequency distribution.

6. The culture evaluation system according to claim 5, wherein the number of cells corresponding to each number of cell divisions is a converted numerical value converted into a state of starting a culturing process.

7. The culture evaluation system according to claim 2, wherein the processor is configured to:
  divide the image into a plurality of regions and acquires the number of cell divisions experienced by each cell within each region, and
  calculate a representative value of the number of cell divisions in each region, and creates a frequency distribution indicating the number of regions for each of the representative values as the frequency distribution.

8. The culture evaluation system according to claim 2, further comprising:
  a storage that stores reference data of the statistical value; and
  a display that displays the statistical value and the reference data in a comparable manner.

9. The culture evaluation system according to claim 8, wherein
  the image sensor sequentially acquires images within the culture container, and
  the processor is configured to:
    calculate a temporal change in the statistical value, and
    control the display to display the temporal change in the statistical value and the reference data in a comparable manner.

10. The culture evaluation system according to claim 8, wherein the processor is further configured to determine the differentiation potency of each cell within the culture container based on a comparison between the statistical value and the reference data.

11. The culture evaluation system according to claim 8, wherein the storage further stores the statistical value.

12. The culture evaluation system according to claim 10, wherein
  the reference data includes a lower limit value and an upper limit value set for the statistical value, and the processor is configured to determine the differentiation potency of each cell within the culture container based on a comparison result of the statistical value compared with the upper limit value and the lower limit value.

13. The culture evaluation system according to claim 12, wherein the display displays an acceptable range defined by the lower limit value and the upper limit value.

14. The culture evaluation system according to claim 10 further comprising:

an evaluation input device to which an evaluation result of cultured cells is input by an operator, wherein the storage stores the evaluation result input to the evaluation input device in association with the statistical value calculated in a culturing process of the evaluated cells.

15. The culture evaluation system according to claim 14, wherein the processor is configured to determine the differentiation potency of each cell within the culture container based on a comparison between a current statistical value of each cell within the culture container and the statistical value which is stored in the storage in association with the evaluation result and which is acquired in a past culturing process.

16. The culture evaluation system according to claim 12, the processor is further configured to:

predict a future statistical value based on a current statistical value obtained from the image of the cells within the culture container, and determine the differentiation potency of each cell in the future based on a comparison result of the future statistical value compared with the lower limit value and the upper limit value.

17. A method for culture evaluation, the method comprising:

acquiring an image of cells cultured within a culture container;

analyzing the image and acquiring the number of cell divisions experienced by each cell in the image; and calculating a statistical value indicating differentiation potency of each cell in the image based on the number of cell divisions acquired by analyzing the image, the differentiation potency being an ability of each cell in the image to be changed into different types of cells and the number of cell divisions being how many times each cell in the image has experienced division, wherein the calculating the statistics includes creating a frequency distribution of the number of cell divisions, and the statistical value represents a bias in the frequency distribution.

* * * * *